United States Patent [19]
Rokach et al.

[11] 4,282,365
[45] Aug. 4, 1981

[54] DIBENZ[B,E]OXEPIN COMPOUNDS

[75] Inventors: Joshua Rokach, Chomedey-Laval, Canada; Edward J. Cragoe, Jr., Lansdale; Clarence S. Rooney, Worcester, both of Pa.

[73] Assignee: Merck & Co., Inc., Rahway, N.J.

[21] Appl. No.: 963,705

[22] Filed: Nov. 24, 1978

[51] Int. Cl.³ ............... C07P 313/12; C07D 233/40; C07D 405/10
[52] U.S. Cl. .................. 548/252; 548/135; 548/253; 548/336; 260/326.5 S; 260/326.5 FM; 260/333; 260/340.9 R; 424/269; 424/273 P; 424/274; 424/278
[58] Field of Search ............ 260/308 D, 333, 306.8 P, 260/326.36, 340.9 R; 548/250, 252, 333, 135; 424/269, 275

[56] References Cited

U.S. PATENT DOCUMENTS 3,706,768   12/1972   Bays .................... 548/252

FOREIGN PATENT DOCUMENTS 1119329   7/1968   United Kingdom .................... 260/333

OTHER PUBLICATIONS

Yoshioka et al., J. of Med. Chem., 21, pp. 633-639 (1978).

Primary Examiner—Donald G. Daus
Assistant Examiner—D. B. Springer
Attorney, Agent, or Firm—Hesna J. Pfeiffer; Thomas E. Arther; Frank M. Mahon

[57] ABSTRACT

Novel dibenz[b,e]oxepin derivatives are employed in the treatment and control of allergic conditions such as allergic asthma.

17 Claims, No Drawings

DIBENZ[B,E]OXEPIN COMPOUNDS

This invention relates to new and useful compositions of matter classifiable in the field of organic chemistry as dibenzoxepins. More particularly, the instant invention relates to a novel group of 6,11-dihydrodibenz[b,e]oxepins; to methods for preparing such compounds; and to the method of employing these and related compounds in the treatment and control of allergic conditions such as asthma.

In its method of treating aspect, therefore, the instant invention may be described as residing in the concept of a method for the treatment and control of allergic conditions such as asthma in a host in need of such treatment which comprises administering to such host pharmaceutical formulations in unit dosage form containing as the essential active ingredient a therapeutically effective amount of an isomeric 6,11-dihydrodibenz[b,e]oxepin characterized by having the structural formulae:

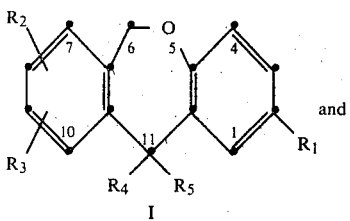

and

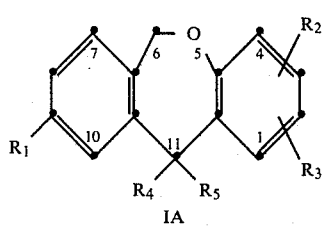

wherein $R_2$ and $R_3$ are the same or different and are members selected from the group consisting of hydrogen, halogen, nitro, amino, N-lower alkylamino N,N-dilower alkylamino, lower alkanoyl, hydroxy, lower alkoxy, lower alkylthio, trifluoromethylthio, lower alkylsulfinyl, lower alkylsulfonyl and trifluoromethyl, and, where $R_2$ and $R_3$ are on adjacent carbon atoms at positions 8 and 9 or 2 and 3, $R_2$ and $R_3$, taken together, are methylenedioxy; $R_4$ is a member selected from the group consisting of hydrogen, hydroxy, loweralkoxy, lower alkylthio, lower alkylsulfinyl, lower alkylsulfonyl, arylthio, amino, formamido and imidazolyl; $R_5$ is a member selected from the group consisting of hydrogen and lower alkyl; $R_4$ and $R_5$, taken together, are a member selected from the group consisting of $=O$ and $=CH-R_7$ wherein $R_7$ is a member selected from the group consisting of hydrogen and aryl; and $R_1$ is a member selected from the group consisting of 5-tetrazolyl, 3-hydroxy-1,2,5-thiadiazol-4-yl, 4-hydroxy-$\Delta^3$-pyrroline-2,5-dione-3-yl or

wherein $R_6$ is a member selected from the group consisting of hydroxy, lower alkoxy, N,N-diloweralkylaminoloweralkoxy, hydroxy lower alkoxy, carboxy lower alkoxy, amino, N-loweralkylamino, N,N-diloweralkylamino, loweralkylsulfonylamino, carboxyloweralkylamino, carboxamidoloweralkylamino or 2-imino-3-methylthiazolidine; and the pharmaceutically acceptable salts thereof.

In its composition of matter aspect, the instant invention may be described as residing in the concept of isomeric 6,11-dihydrodibenz[b,e]oxepins characterized by having structural formulae I and IA, above, wherein $R_1$, $R_2$, $R_3$, $R_4$ and $R_5$ are as defined therein, with the proviso that $R_1$ is not 5-tetrazolyl, carboxy or carboxamido when $R_4$ and $R_5$, taken together are $=O$ and $R_2$ and $R_3$ are hydrogen. Compounds in which $R_1$ is 5-tetrazolyl, carboxy or carboxamido, $R_4$ and $R_5$, taken together, are $=O$ and $R_2$ and $R_3$ are hydrogen are known in the prior art as antiinflammatory agents (see J. Med. Chem., Vol. 21, NO. 7, pp. 633–639, 1978). Such compounds form no part of the composition of matter aspect of the instant invention.

As used herein, the term, halogen, includes chlorine, bromine, iodine and fluorine. The terms lower alkyl and lower alkoxy, wherever employed, and unless otherwise specified, include straight and branched chain alkyl and alkoxy groups having 1 to 4 carbon atoms in the alkyl or alkoxy moiety such as, for example, methyl, ethyl, isopropyl, butyl, ethoxy, propoxy and isobutoxy. The term, lower alkanoyl includes straight and branched chain alkanoyl groups of 1 to 4 carbon atoms including, for example, formyl, acetyl, propanoyl and butyryl. The term, aryl, is intended to include phenyl and ring substituted phenyl such as, for example, ortho-, meta-, and para-lower alkylphenyl, ortho-, meta-, and para-halophenyl, ortho-, meta- and para-hydroxyphenyl, ortho-, meta-, and para-lower alkoxyphenyl, ortho-, meta-, and para-lower alkanoylphenyl, ortho-, meta-, and para-nitrophenyl, ortho-, meta-, and para-lower alkylthipphenyl, ortho-, meta- and para-trifluoromethylphenyl and the like.

The instant invention is based upon applicants' discovery that the oxepins of Formula I and IA, above, markedly antagonize the actions of contractile prostaglandins such as $PGF_{2\alpha}$, $PGG_2$, $PGH_2$ and $TXA_2$. The use of the oxepins of this invention, which act as prostaglandin antagonists, and biosynthesis inhibitors, offers a new approach to therapy in a variety of allergic conditions such as allergic asthma where excessive contractile activity of prostaglandins and prostaglandin biosynthetic intermediates occur. It is well known, for example, that prostaglandins such as $PGF_{2\alpha}$, $PGG_2$, $TXA_2$* and $PGH_2$ are potent contractants of bronchial muscle and that human asthmatics are especially sensitive to the bronchial constricting action of $PGF_{2\alpha}$. The antagonizing action of the oxepins of this invention against the constricting actions of contractile prostaglandins has been confirmed in vitro and in vivo using standard pharmacological techniques. It is contemplated, therefore, that the oxepins of this invention will be employed in dosage unit form as the essential active ingredient in pharmaceutical formulations intended for the treatment and control of allergic conditions such as asthma in humans and warm blooded animals.

*$TXA_2$ is the commonly used abbreviation for thromboxan-$A_2$.

The novel 6,11-dihydro-11-oxidibenz[b,e]oxepins of this invention, conveniently, are prepared from the 2-(or 9)-cyano intermediates having the following structural formulae:

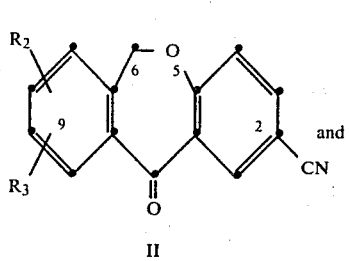

II

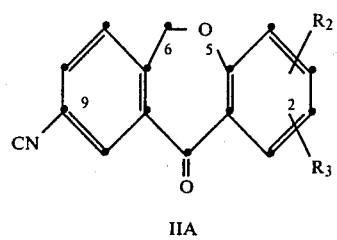

IIA wherein $R_2$ and $R_3$ are as previously defined. These 2-(or 9)-cyano-6,11-dihydro-11-oxodibenz[b,e]oxepin intermediates are themselves readily prepared from well known starting materials which are either available commercially or may be prepared by conventional techniques already fully described in the chemical literature.

Thus, 2-cyano-6,11-dihydro-11-oxodibenz[b,e]oxepin (II) may be prepared according to the following general reaction scheme:

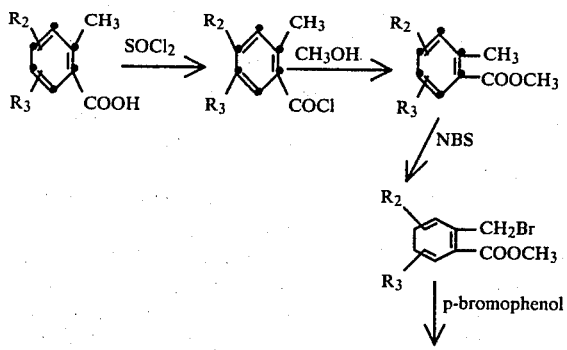

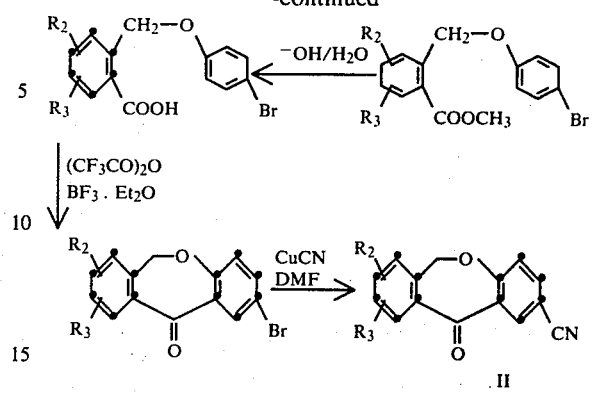

wherein $R_2$ and $R_2$ are as previously defined, by treating an appropriately substituted $R_2$ and/or $R_3$ o-toluic acid with thionyl chloride in order to obtain the corresponding acid chloride which then is treated with methanol (or any desired lower alkanol) in order to obtain the corresponding methyl (or lower alkyl) ester. The ester then is refluxed with N-bromosuccinimide to form the corresponding methyl (or lower alkyl) α-bromo-o-toluate which is reacted with p-bromophenol in order to obtain the corresponding methyl (or lower alkyl) o-(p-bromophenoxymethyl)benzoate. Hydrolysis of this compound yields the corresponding o-(p-bromophenoxymethyl)benzoic acid. Cyclization of the acid with trifluoroacetic anhydride in the presence of boron trifluoride-ether complex yields the corresponding 2-bromo-6,11-dihydro-11-oxodibenz[b,e]oxepin. The cyano group is introduced by treating the 2-bromo compound under reflux in N,N-dimethylformamide with cuprous cyanide to form the desired $R_2$ and/or $R_3$ substituted 2-cyano-6,11-dihydro-11-oxodibenz[b,e]oxepin of Formula II.

9-Cyano-6,11-dihydro-11-oxodibenz[b,e]oxepin (IIA) may be prepared according to the following general reaction scheme:

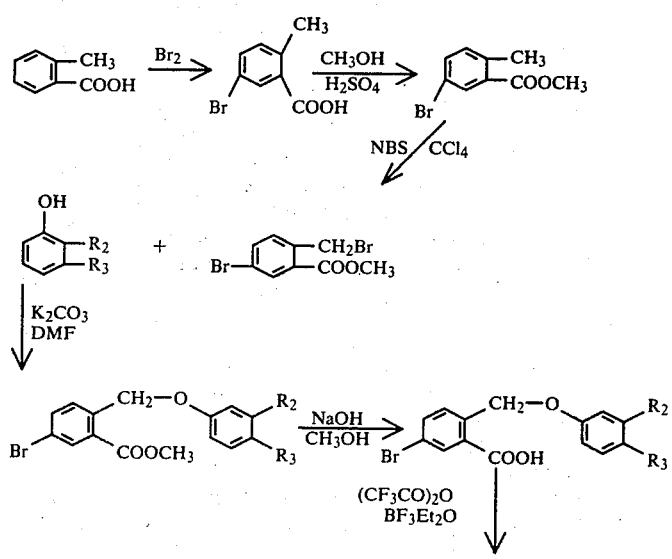

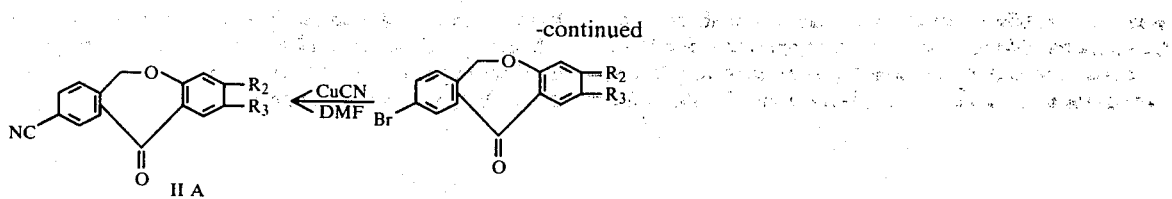

wherein $R_2$ and $R_3$ are as previously defined, by reacting o-toluic acid with bromine in the presence of iron powder in order to obtain 5-bromo-o-toluic acid. The product obtained from the reaction mixture is predominately the desired 5-bromo isomer although some 3-bromo isomer may be present. If desired, pure 5-bromo isomer can be separated by conventional techniques and employed in pure form as the starting material for subsequent steps. Separation, however, is unnecessary and the product obtained from the reaction mixture usually is employed in the next step without further purification. The 5-bromo acid then is treated with methanol (or any desired lower alkanol) in the presence of a strong acid such as sulfuric acid to form methyl (or lower alkyl) ester which then is treated with N-bromosuccinimide in the presence of benzoyl peroxide under reflux to form methyl (or lower alkyl) α,5-dibromo-o-toluate. The dibromo ester then is reacted with an appropriately substituted $R_2$ and/or $R_3$ phenol in the presence of dimethylformamide and potassium carbonate to obtain the corresponding methyl (or lower alkyl) 5-bromo-α-($R_2$ and/or $R_3$ substituted phenoxy)-o-toluate. Hydrolysis of the ester with methanol and sodium hydroxide yields, on acidification, the free acid when is cyclized in the presence of trifluoroacetic anhydride and boron trifluoride-ethyl ether complex to form the corresponding 9-bromo-6,11-dihydro-11-oxodibenz[b,e]oxepin. The cyano group is introduced as previously described by treating the 9-bromo compound with cuprous cyanide in the presence of dimethylformamide in order to obtain the desired $R_2$ and/or $R_3$ substituted 9-cyano-6,11-dihydro-11-oxodibenz[b,e]oxepin of formula IIA.

The novel 6,11-dihydro-11-oxidibenz[b,c]oxepins of the instant invention wherein the substituent at the 2- (or 9)-position is carboxy are prepared by refluxing the 2- (or 9)-cyano intermediates of formula II or IIA in a mixture of aqueous hydrochloric acid and glacial acetic acid. The reaction usually requires from 18 to 160 hours for completion and the desired 6,11-dihydro-11-oxodibenz[b,e]oxepin-2- (or 9)-carboxylic acid of formula III or IIIA is recovered from the reaction mixture upon cooling.

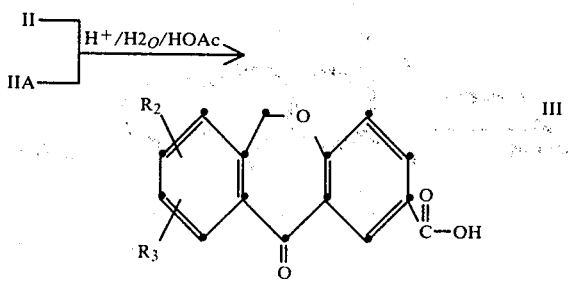

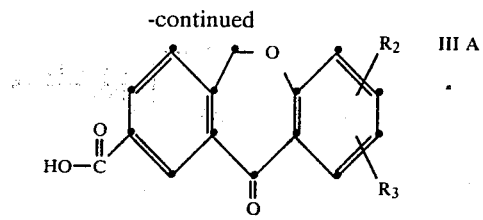

The novel 6,11-dihydro-11-oxibenz[b,e]oxepins of this invention wherein the substituent at the 2- (or 9)-position is 5-tetrazolyl also are prepared from the 2- (or 9)cyano intermediates of formula II or IIA. The nitrile is heated in a mixture of sodium azide and ammonium chloride in a suitable organic solvent such as dimethylformamide. Conveniently, the reaction is carried out at reflux and usually requires 4 to 30 hours for completion. After dilution with excess water or with excess sodium carbonate and extraction with ethyl acetate, the aqueous phase is acidified to obtain the desired 2- (or 9)-(1H-tetrazol-5-yl)-6,11-dihydro-11-oxodibenz[b,e]oxepin of formula IV or IVA.

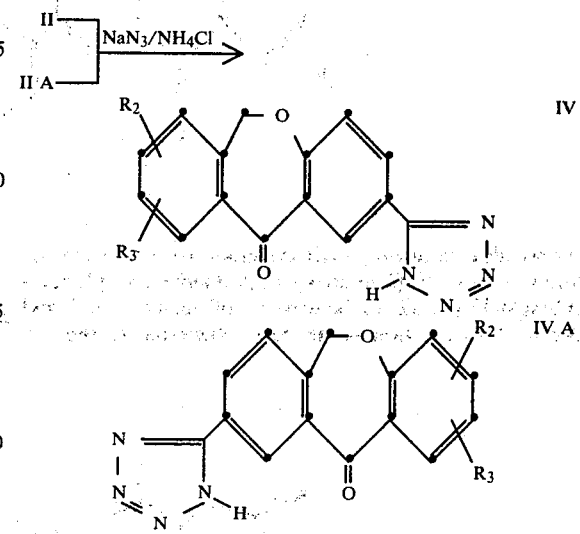

Those 6,11-dihydro-11-oxodibenz[b,e]oxepins of this invention wherein the substituent at the 2- (or 9)-position is 3-hydroxy-1,2,5-thiadiazol-4-yl are prepared by refluxing the 2- (or 9)-cyano intermediate of formula II or IIA in formic acid in the presence of Raney nickel alloy for 1 to 2 hours in order to obtain the corresponding 6,11-dihydro-11-oxodibenz[b,e]oxepin-2- (or 9)-carboxaldehyde. The aldehyde product then is converted into the corresponding 2- (or 9)-(2-aminoacetonitrile) by treatment with sodium cyanide in an alcoholic solvent saturated with ammonia and in the presence of ammonium chloride and ammonium hydroxide. The reaction usually is conducted at room temperature and requires from 8 to 16 hours for completion. The aminoacetonitrile so produced is treated with concentrated hydrochloric acid at room temperature for 20 to 45 minutes in order to obtain the corresponding 2- (or 9)-(2-aminoacetamide) which then is treated with sulfur monochloride in dimethylformamide to obtain the desired 2- (or 9)-(3-hydroxy-1,2,5-thiadiazol-4-yl)-6,11-dihydro-11-oxodibenz[b,e]oxepin of formula XX and XXA. This reaction sequence is illustrated in the following diagram, it being understood that position of the 3-hydroxy-1,2,5-thiadiazol-4-yl substituent in the final product depends upon the selection of the appropriate 2- (or 9)-cyano starting material.

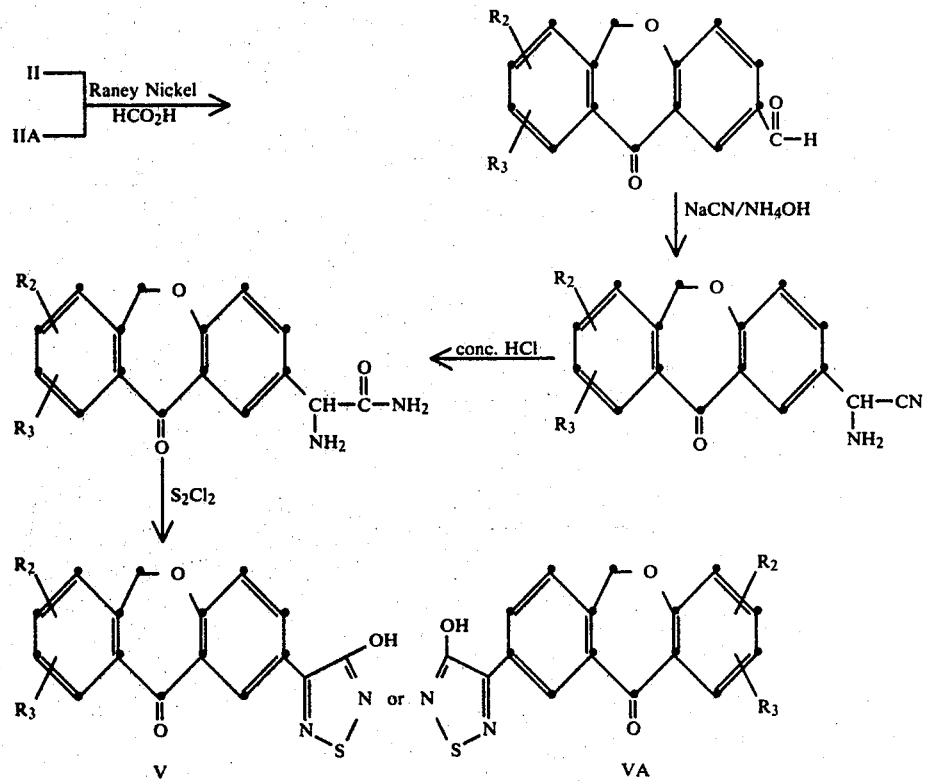

Those 6,11-dihydro-11-oxodibenz[b,e]oxepins of this invention wherein the substituent at the 2-position is 4-hydroxy-3-pyrrolin-2,5-dione-3-yl may be prepared according to the following general reaction scheme:

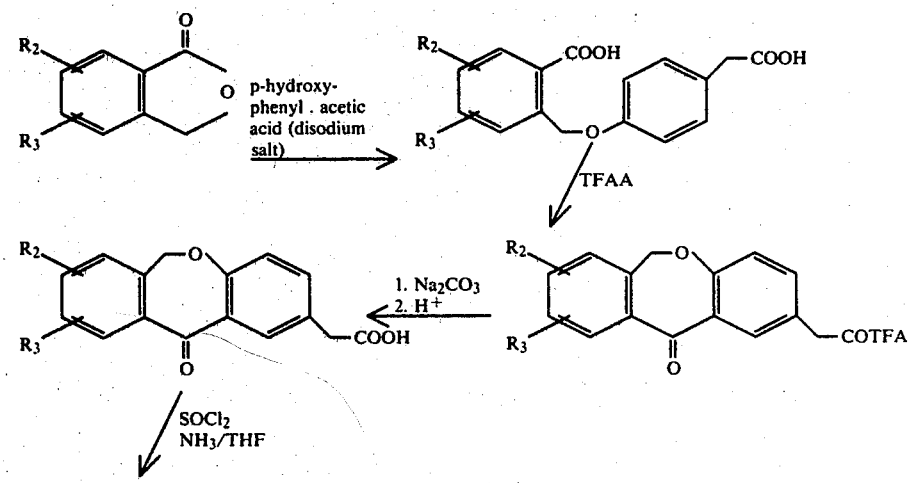

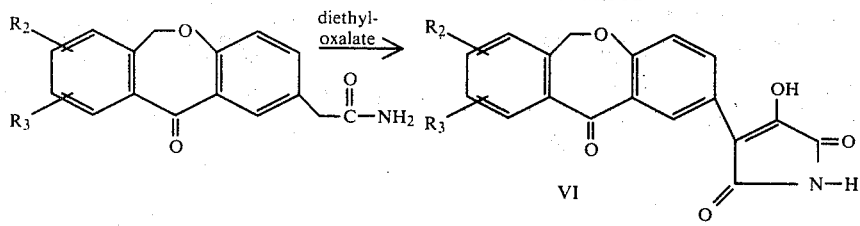

wherein $R_2$ and $R_3$ are as previously defined, by treating an appropriately substituted $R_2$ and/or $R_3$ phthalide with the disodium salt of p-hydroxyphenylacetic acid at 170°–250° C. for 2–3 hours to obtain the corresponding 4-(2-carboxybenzyloxy)phenylacetic acid. The disodium salt of p-hydroxyphenylacetic acid is formed by treating the acid with aqueous sodium hydroxide and evaporating the mixture to dryness. The phthalide is then added and the reaction is carried out as described above. The carboxybenzyloxyphenylacetic acid so produced then is cyclized by stirring with trifluoroacetic anhydride in a pressure bottle at 70°–80° C. for 1–3 hours. The intermediate $R_2$ and/or $R_3$ substituted 6,11-dihydro-11-oxodibenzo[b,e]oxepin-2-acetic acid trifluoroacetic acid mixed anhydride then is treated with base and acidified in order to obtain the free acid. The free acid then is treated with thionyl chloride followed by ammonia to form the corresponding acetamide which is treated with diethyl oxalate in dimethylformamide in the presence of potassium t-butoxide to form the desired $R_2$ and/or $R_3$ substituted 2-(4-hydroxy-$\Delta^3$-pyrrolin-2,5-dione-3-yl)-6,11-dihydro-11-oxodibenz[b,e]oxepin of formula VI.

The 6,11-dihydro-11-oxodibenz[b,e]oxepins of this invention wherein the substituent at the 9-position is 4-hydroxy-$\Delta^3$-pyrrolin-2,5-dione-3-yl may be prepared according to the following general reaction scheme:

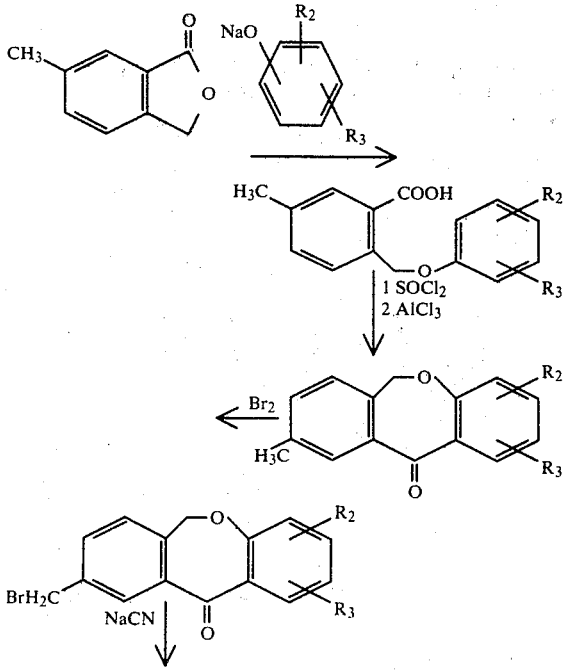

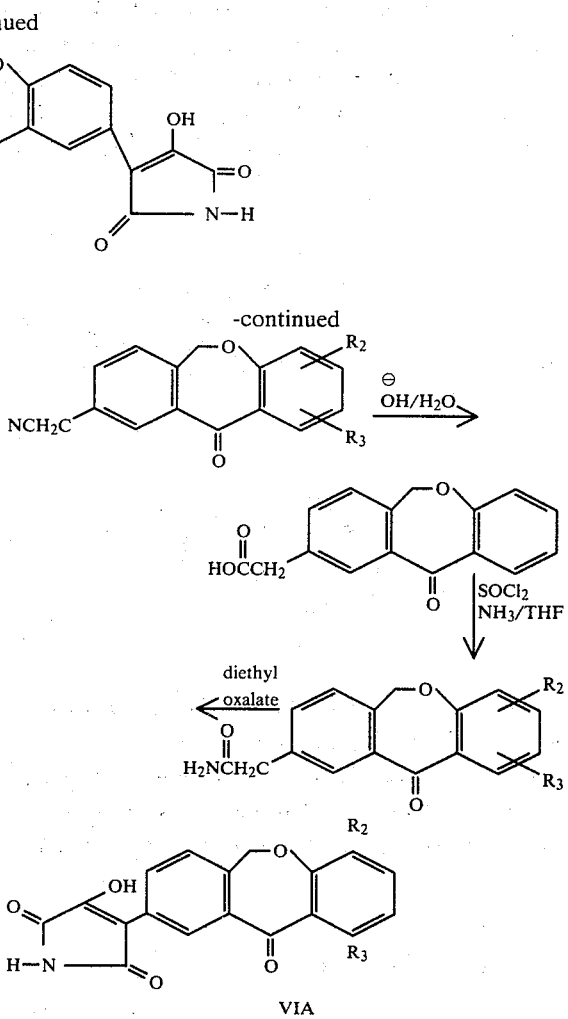

wherein $R_2$ and $R_3$ are as previously defined, by treating 6-methylphthalide with an appropriately substituted $R_2$ and/or $R_3$ substituted sodium phenolate at a temperature of 190°–230° C. for 0.5–3 hours to obtain the corresponding 2-phenoxymethyl-5-methylbenzoic acid which is treated with thionyl chloride and cyclized in the presence of aluminum chloride to form the corresponding 9-methyl-6,11-dihydro-11-oxodibenz[b,e]oxepin. The 9-methyl derivative then is brominated and the bromomethyl compound so produced is treated with sodium cyanide to form the corresponding 9-cyanomethyl derivative. This intermediate then is hydrolyzed to the corresponding 9-acetic acid derivative which is treated with thionyl chloride followed by ammonia to form the corresponding 9-acetamide derivative by techniques already described. The acetamide then is treated with diethyl oxalate in dimethylformamide in the presence of potassium t-butoxide to form the desired 9-(4-hydroxy-$\Delta^3$-pyrrolin-2,5-dione-3-yl)-6,11-dihydro-11-oxodibenz[b,e]oxepin of formula VIA.

In addition to their therapeutic properties as noted above, the 2-(or 9)-carboxylic acid derivatives of this invention serve as valuable intermediates in the preparation of other $R_1$ substituted 6,11-dihydro-11-oxodibenz[b,e]oxepins of formula I and IA. Thus, the 2-(or 9) carboxylic acid of formula (III or IIIA) may be converted readily into the corresponding acid halide, preferably the acid chloride, by treating the carboxylic acid with a thionyl halide, preferably thionyl chloride. The resulting 2-(or 9)-halocarbonyl-6,11-dihydro-11-oxodibenz[b,e]oxepin (i.e., the 2-(or 9)-chlorocarbonyl compounds of formula VII or VIIA) then may be treated with various well-known reagents to form desired ester and amide derivatives.

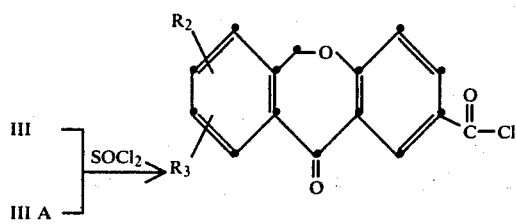

Thus, for example, the chlorocarbonyl compounds of formula VII and VIIA may be treated:

(a) with a lower alkanol such as, for example, methanol, ethanol, 2-propanol, butanol and 2-butanol, to form the corresponding loweralkyl esters, VII and VIIA:

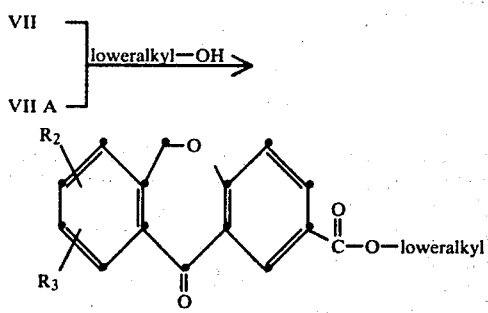

(b) with ammonia to form the corresponding carboxamides, IX and IXA:

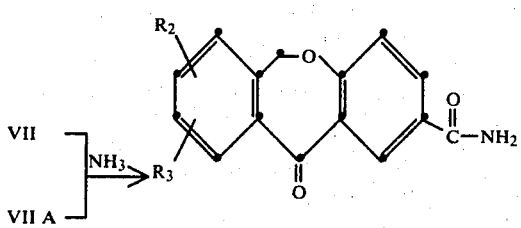

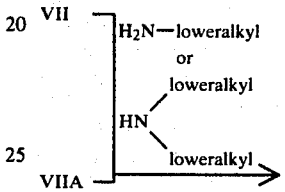

(c) with an N-loweralkylamine such as, for example, methylamine, ethylamine, propylamine, isopropylamine and butylamine, or an N,N-diloweralkylamine such as, for example, dimethylamine, diethylamine, dipropylamine and dibutylamine, to form the corresponding N-loweralkylcarboxamide X or XA, or N,N-diloweralkylcarboxamide, XI or XIA:

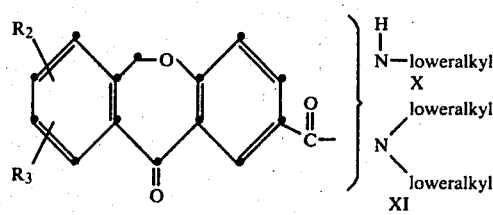

(d) with lower alkylsulfonamide to form the corresponding N-lower alkylsulfonyl-carboxamide, XII and XIIA:

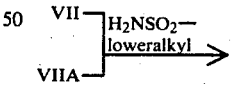

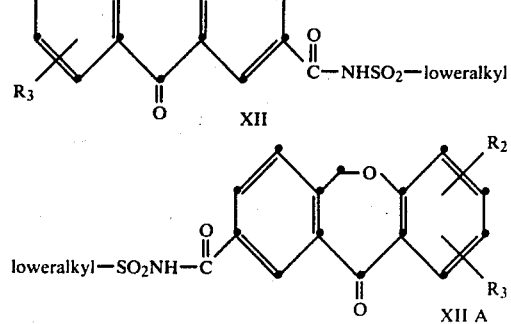

(e) with 2-imino-3-methylthiazolidine to form the corresponding (3-methyl-2-thiazolidinylidene)carboxamide, XIII and XIIIA:

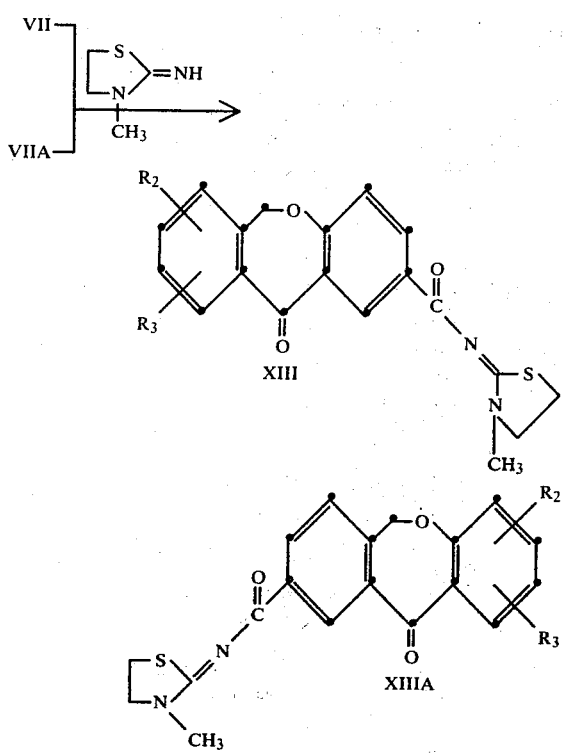

(f) with a loweralkyldiol such as, for example, ethylene glycol, trimethylene glycol and, 4-butanediol, to form the corresponding hydroxyloweralkylester, XIV and XIVA:

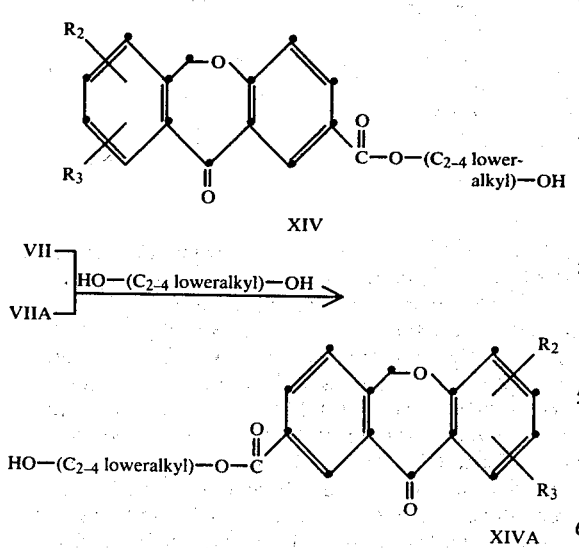

(g) with an N,N-diloweralkylaminoloweralkanol such as, for example, N,N-dimethylethanolamine, N,N-diethylethanolamine, 3-(N,N-dimethylamino)propan-1-ol and 4-(N,N-diethylamino)butan-1-ol, to form the corresponding N,N-diloweralkylaminoloweralkyl ester XVII and XVIIA:

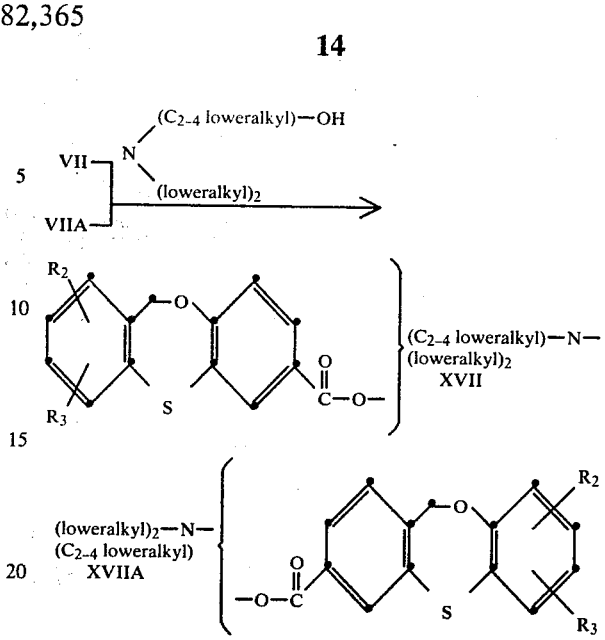

(h) with an amino acid such as, for example, glycine, alanine and valine, to form the corresponding N-carboxy-loweralkylcarboxamide, XVIII and XVIIIA:

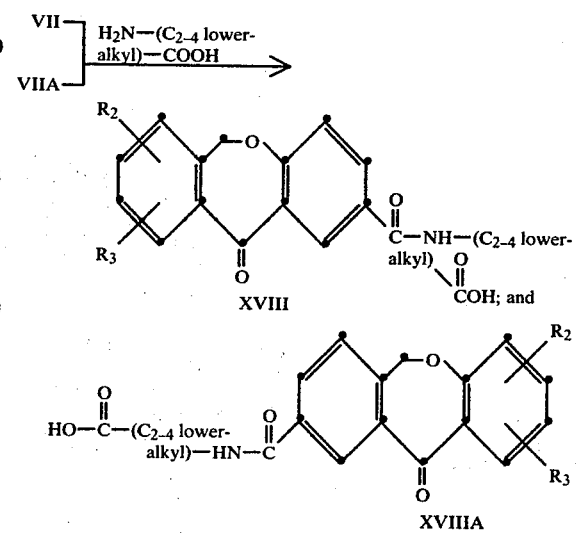

(i) with an alkali metal salt of a hydroxyloweralkanoic acid such as, for example, hydroxyacetic acid, 3-hydroxy-butyric acid and β-hydroxypropionic acid, to form the corresponding carboxyloweralkyl ester, XIX and XIXA:

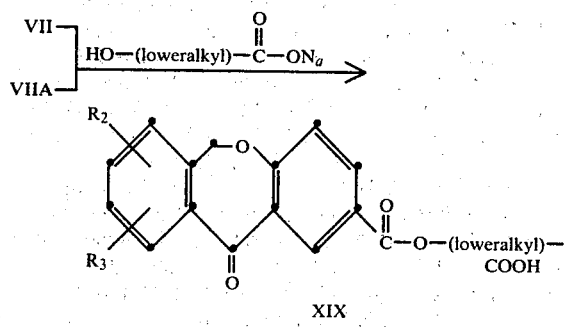

-continued

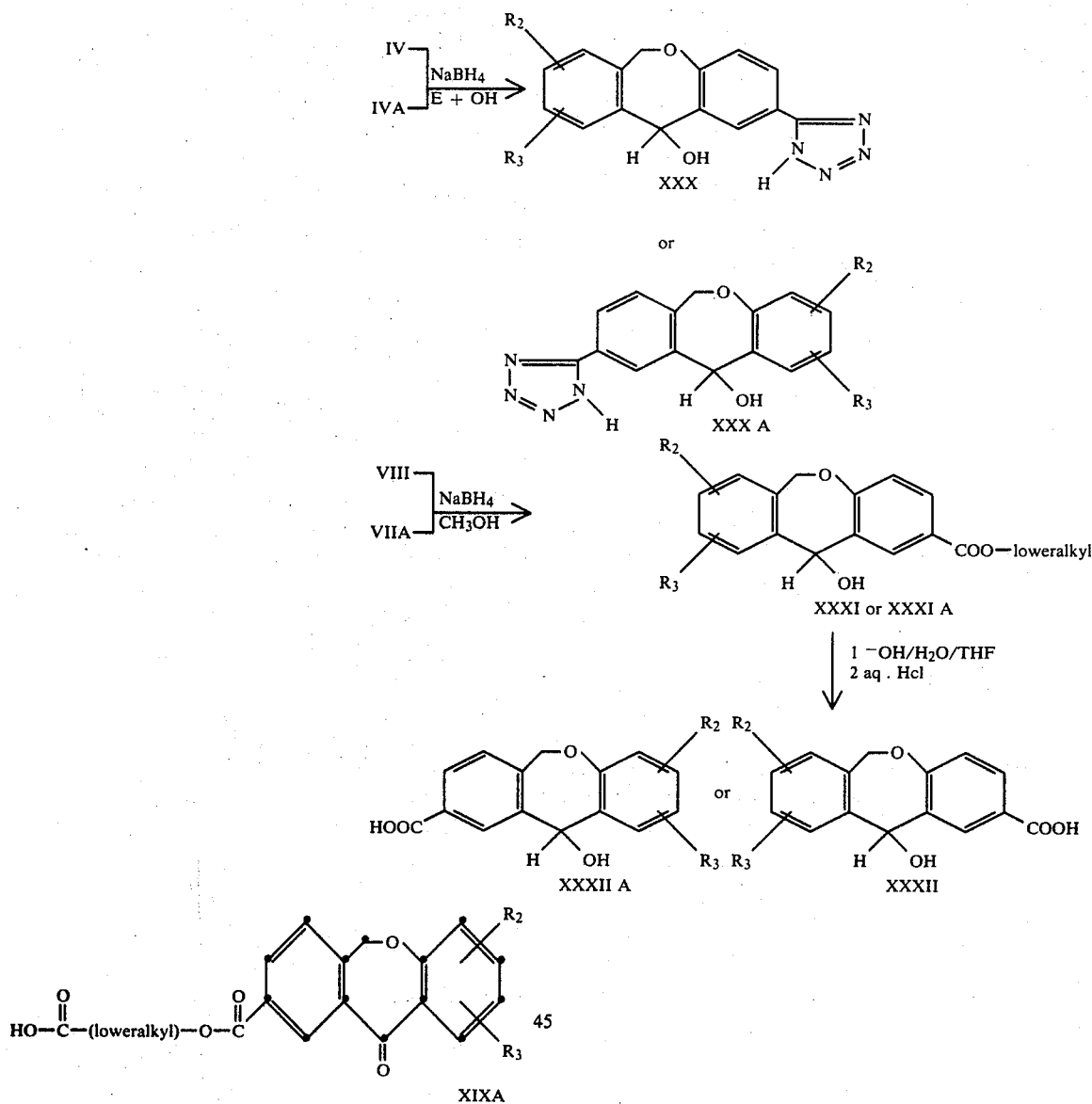

Those 6,11-dihydrodibenz[b,e]oxepins of formula I and IA wherein $R_4$ is hydroxy and $R_5$ is hydrogen (e.g., 6,11-dihydro-11-hydroxydibenz[b,e]oxepins) are readily prepared by treating the corresponding 11-oxo compound ($R_1$, $R_2$ and $R_3$ are as previously defined) with a reducing agent. Thus, for example, the 2-(or 9)-(1H-tetrazol-5-yl)-6,11-dihydro-11-oxodibenz[b,e]oxepins of formula IV or IVA may be treated with sodium borohydride usually at room temperature in a suitable organic solvent such as ethanol. Upon diluting the reaction mixture with water and acidification the desired 2-(or 9)-(1H-tetrazol-5-yl)-6,11-dihydro-11-hydroxydibenz[b,e]oxepin (formula XXX or XXXA) is isolated. Similarly, the 2-(or 9) carboxylic acid of formula III or IIIA, preferably in the form of a lower alkyl ester of formula VIII or VIIIA, may be reduced to the corresponding 11-hydroxy compound from which the ester group is removed by hydrolysis to form the 6,11-dihydro-11-hydroxydibenz[b,e]oxepin 2-(or 9)-carboxylic acid of formula XXXII or XXXIIA. These reactions are illustrated in the following diagram.

The 11-hydroxy compounds of Formula I and IA ($R_1$, $R_2$, and $R_3$ are as previously defined) prepared as described above upon treatment at reflux with thionyl chloride are readily converted to the corresponding 11-chloro compound which serves as an intermediate for the preparation of other 11-substituted compounds of the instant invention. The 11-chloro intermediate may be isolated and employed per se as the starting material for subsequent conversions. If desired, however, the 11-chloro intermediate may be formed in situ and employed in subsequent reactions without isolation.

Thus, for example, the 2-(or 9)-carboxylic acid of Formula III or IIIA, preferably in the form of a lower alkyl ester of Formula VIII or VIIIA, may be refluxed with thionyl chloride in order to form the corresponding 6,11-dihydro-11-chlorodibenz[b,e]oxepin-2-(or 9)-loweralkyl carboxylate. The reaction usually is complete in 5–20 minutes and the product (Formula XXXIII or XXXIIIA) is obtained after removal of the thionylchloride.

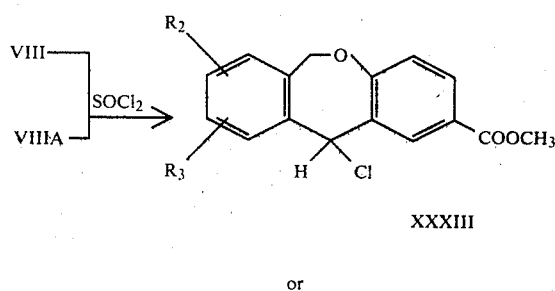

XXXIII or with water, the product is recovered by filtration and purified by conventional recrystallization.

Thus, for example, the 6,11-dihydro-11-chlorodibenz[b,e]oxepin 2-(or 9)-lower alkyl carboxylate of Formula XXXIII or XXXIIIA may be treated with methanesulfinic acid sodium salt in dimethylformamide in order to obtain the corresponding 6,11-dihydro-11-methylsulfonyldibenz[b,e]oxepin 2-(or 9)-lower alkyl carboxylate (Formula XXXIV or XXXIVA) which may be hydrolyzed by conventional techniques in order to obtain the free acid of Formula XXXV or XXXVA.

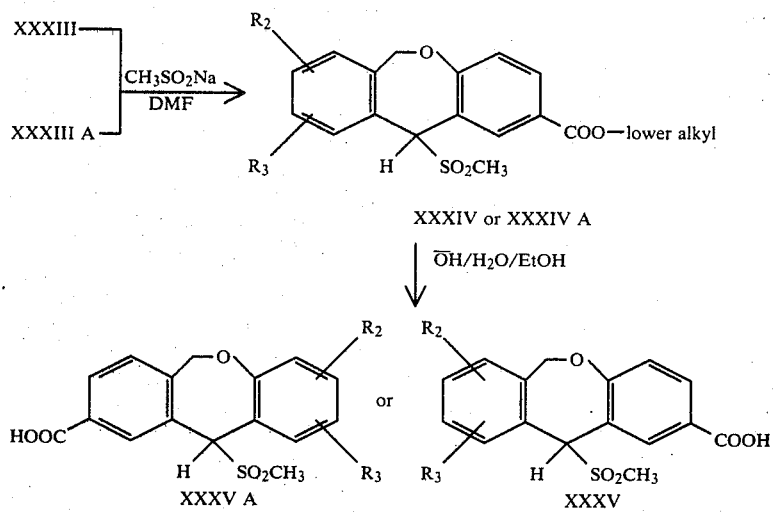

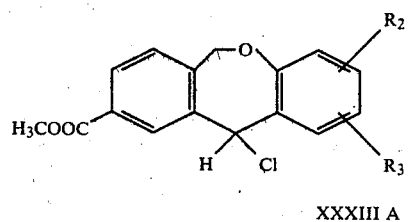

XXXIII A

The 11-lower alkylthio compounds of Formula I and IA (R₁, R₂, and R₃ are as previously defined) may be prepared by treating the corresponding 11-chloro intermediate in dimethylformamide with methanesulfinic acid alkali metal salt, such as the sodium salt. About a 10% excess of the salt is employed and the reaction is run at room temperature. About 3 to about 6 days usually is required to complete the reaction. After dilution Preparation of the 11-loweralkylthio compound of formula I and IA (R₁, R₂ and R₃ are as previously defined) is achieved by treating the corresponding 11-chloro intermediate in dimethylformamide with a lower alkylthiol. The reaction conveniently is run at room temperature and usually requires from 1 to 3 hours for completion. The product is recovered by extraction into ether, washing with base, drying and evaporation to dryness.

Thus, for example, the 6,11-dihydro-11-chlorodibenz[b,e]oxepin-2-(or 9)-lower alkyl carboxylate of formula XXXIII or XXXIII A may be treated in dry dimethylformamide solution with methanethiol at room temperature in order to obtain the corresponding 6,11-dihydro-11-methylthiodibenz[b,e]oxepin-2-(or 9)-lower alkyl carboxylate of formula XXXVI or XXXVI A. The ester, by conventional hydrolysis, may be converted to the free acid of formula XXXVII or XXXVII A.

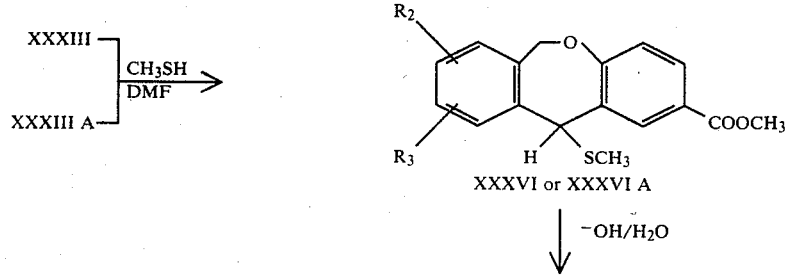

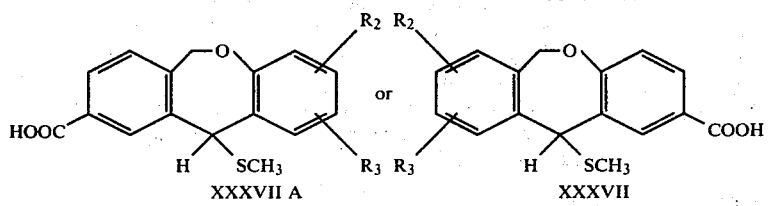

Where 11-aryl thio derivatives are desired, it is necessary only to substitute an arylthiol for the lower alkylthiol employed in the foregoing reaction. Thus, for example, by substituting phenylthiol or a ring substituted phenylthiol, such as for example an ortho-, meta- or para- lower alkyl, halo, hydroxy, lower alkylthio or trifluoromethylphenyl thiol for the lower alkyl thiol employed above the corresponding 11-phenylthio 11-substituted phenylthio compounds are obtained.

Oxidation of the 11-lower alkylthio compounds described above affords the corresponding 11-lower alkylsulfinyl derivatives of Formula I or IA ($R_1$ and $R_3$ are as described above). The 11-lower alkylthio compounds may be oxidized with hydrogen peroxide in the presence of an acidic solvent such as acetic acid or with organic peroxides such as peroxy acids including, for example, m-chloroperbenzoic acid and the like. A 1:1 molar ratio of oxidant to reductant produces the desired lower alkylsulfinyl compound. For example, the 6,11-dihydro-11-methylthiodibenz[b,e]oxepin-2-(or 9)-carboxylic acid of formula XXXVII and XXXVII A in acetic acid solution may be treated with 30% hydrogen peroxide to obtain the corresponding 6,11-dihydro-11-methylsulfinyl dibenz[b,e]oxepin-2-carboxylic acid of formula XXXVIII and XXXVIII A.

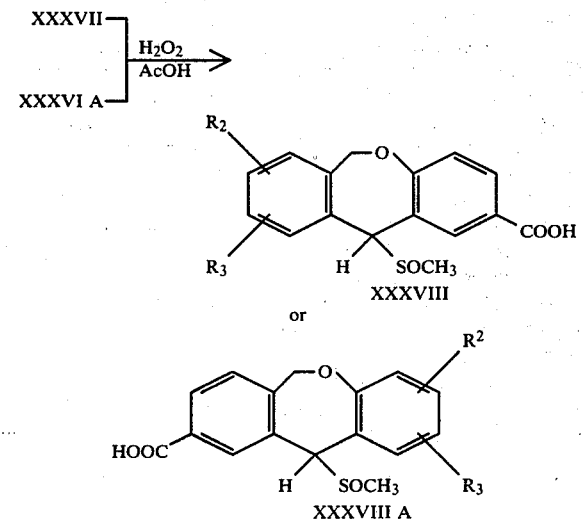

In a similar manner, the 11-chloro intermediate of formula I and I A ($R_1$, $R_2$ and $R_3$ are as previously defined) may be treated with methanethiol potassium salt (formed in situ from potassium tert-butoxide and methanethiol); with a loweralkanol, such as for example methanol, ethanol, propanol, iso-propanol, n-butanol and the like, in the presence of potassium tert-butoxide; and with imidazole to form, respectively, the corresponding 11-unsubstituted ($R_4$ and $R_5$ are hydrogen), the 11-lower alkoxy and the 11-imidazolyl compounds of formula I and I A.

The 11-chloro intermediate of formula I and IA ($R_1$, $R_2$ and $R_3$ are as previously defined) also may be treated with formamide in order to obtain the corresponding 11-formamido compound which then may be subjected to conventional hydrolysis to obtain the corresponding 11-amino compound. Thus, for example, the 6,11-dihydro-11-chlorodibenz[b,e]oxepin-2-(or 9)-lower alkyl carboxylate of formula XXXIII or XXXIIIA may be heated with formamide at 100° to 120° C. for 2–4 hours, cooled, diluted with water and filtered to obtain the corresponding 6,11-dihydro-11-formamidodibenz[b,e]oxepin-2-(or 9)-lower alkyl carboxylate of formula XXXIX and XXXIXA. Acid hydrolysis of these compounds, where desired, yields the 11-amino compounds. Where the hydrolysis is carried out under mild conditions (dilute aqueous acid such as 5–15% hydrochloric acid and moderate temperature such as 35°–50° C.), hydrolysis occurs on at the 11-formamido group resulting in the formation of the corresponding 6,11-dihydro-11-aminodibenz[b,e]oxepin-2-(or 9)-lower alkyl carboxylate of formula XL and XLA. Under more vigorous conditions (concentrated acid such as concentrated hydrochloric acid and more elevated temperatures such as 80° to 100° C.), hydrolysis occurs at both the formamido group and the ester group resulting in the formation of the corresponding 6,11-dihydro-11-aminodibenz[b,e]oxepin-2-(or 9)-carboxylic acid of formula XLI and XLIA. Regeneration of the formamido group on the free amino acid is readily achieved by treating the free amino acid with formicacetic anhydride in the presence of formic acid which results in the formation of the corresponding 6,11-dihydro-11-formamido[b,e]oxepin-2-(or 9)-carboxylic acid of formula XLII or XLIIA.

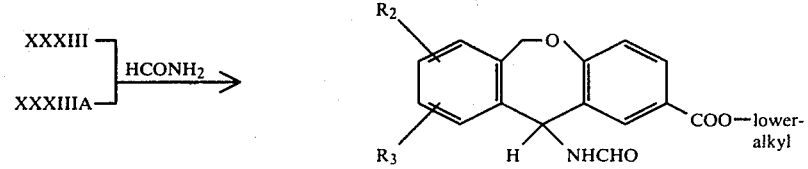

-continued

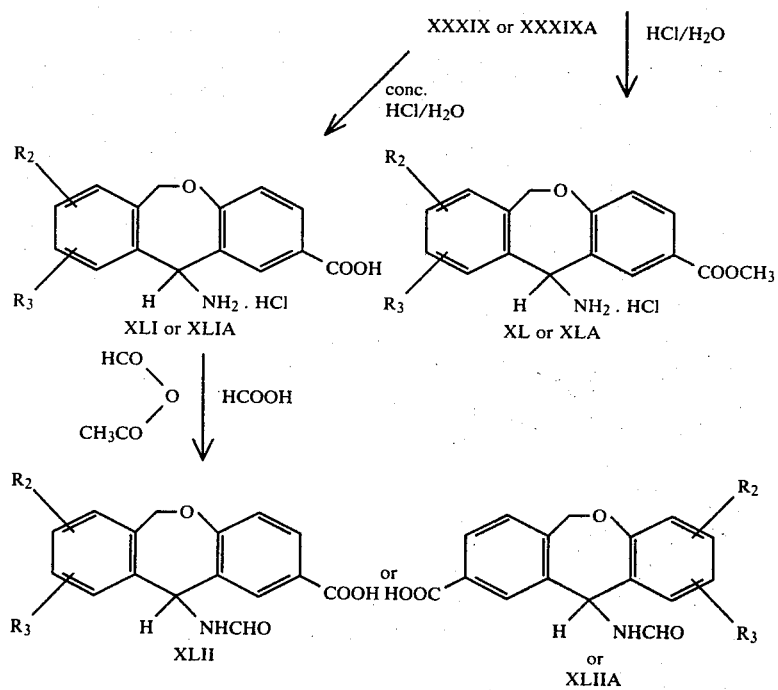

The 11-hydroxy-11-loweralkyl compounds of formula I and Ia ($R_1$, $R_2$ and $R_3$ are as previously defined) may be prepared by treating the corresponding 2-(or 9)-carboxylic acid, preferably in the form of a lower alkyl ester, with a suitable Grignard reagent such as for example methyl magnesium iodide, ethyl magnesium bromide, iso-propyl magnesium iodide, propyl magnesium iodide, n-butyl magnesium bromide and the like, and hydrolyzing the resulting lower alkyl carboxylate to form the free acid. Thus, for example, the 6,11-dihydro-11-oxodibenz[b,e]2-(or 9)-lower alkyl carboxylate of formula VIII or VIIIA may be treated with methyl magnesium iodide to form the corresponding 6,11-dihydro-11-hydroxy-11-lower alkyldibenz[b,e]oxepin-2-(or 9)-lower alkyl carboxylate of formula XLIII or XLIIIA which then is hydrolyzed to form the corresponding 2-(or 9)-carboxylic acid of formula XLIV or XLIVA.

The 11-hydroxy-11-loweralkyl-2-(or 9)-lower alkyl carboxylates as prepared above may be heated with benzene in the presence of p-toluenesulfonic acid to form the corresponding 11-alkylidene-2-(or 9)-lower alkyl carboxylates of formula I or Ia ($R_1$, $R_2$ and $R_3$ are as previously defined) which, upon hydrolysis, yield the corresponding free acids. Reduction of the free acids yield the corresponding 11-methyl compounds. Thus, for example, the 6,11-dihydro-11-hydroxy-11-methyl-dibenz[b,e]oxepin-2-(or 9)-lower alkyl carboxylate of formula XLIII or XLIIIA may be heated with benzene in the presence of p-toluenesulfonic acid to form the corresponding 11-methylene derivative of formula XLV or XLVA which may be hydrolyzed to form the free acids of formula XLVI or XLVIA and then reduced catalytically to form the corresponding 11-methyl derivatives of formula XLVII and XLVIIA.

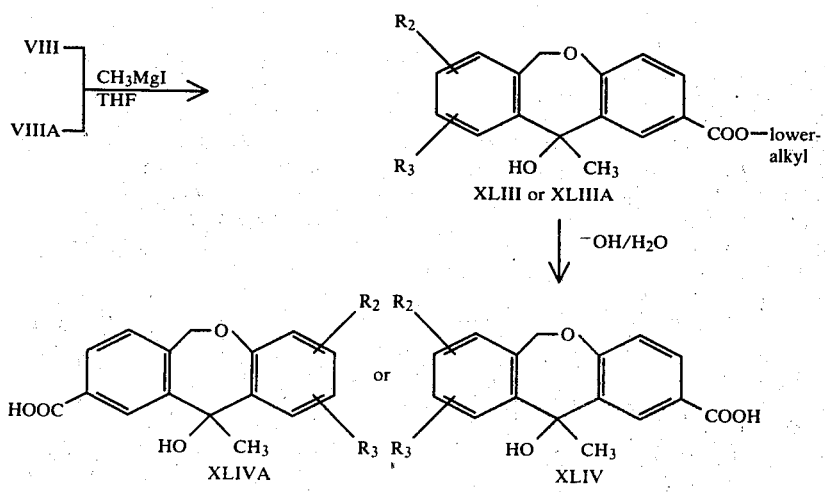

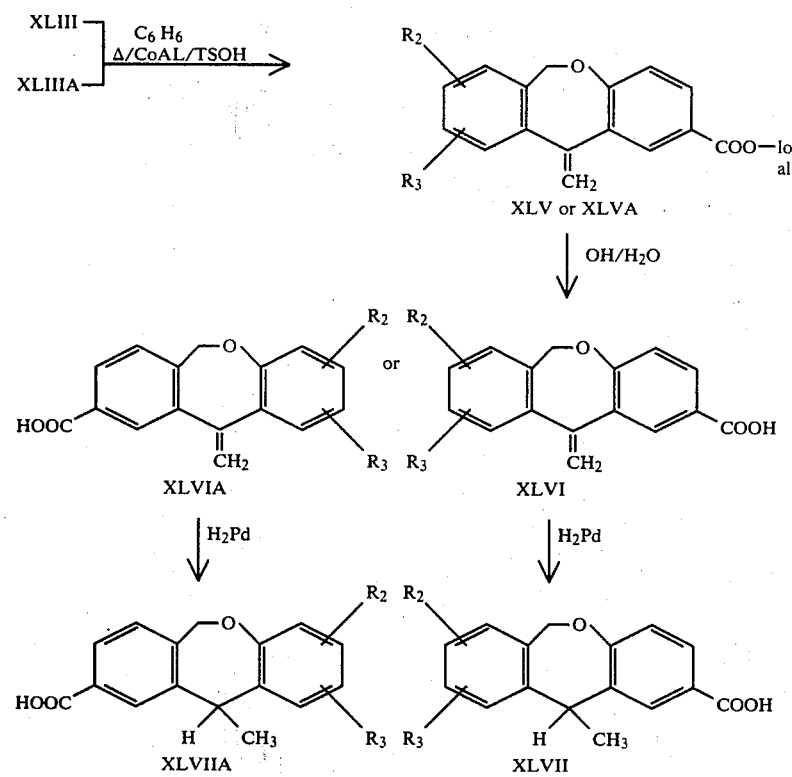

Other 11-lower alkylidene compounds of formula I or IA ($R_1$, $R_2$, and $R_3$ are as previously defined) may be prepared by treating the corresponding 2-(or 9)-cyano-6,11-dihydro-11-oxodibenz[b,e]oxepin of formula II or IIA with a lower alkyl triphenylphosphonium bromide in the presence of tert. butyllithium. The 2-(or 9)-cyano group then may be converted to the 2-(or 9)-carboxylic acid, 2-(or 9)-tetrazolyl or other desired $R_1$ group by methods described above. Substituting a lower alkylphenyl or a ring substituted lower alkylphenyl triphenylphosphonium bromide for the lower alkyl triphenylphosphonium bromide results in the formation of the corresponding 11-phenylloweralkylidene or 11-ring substituted phenylloweralkylidene compounds.

As noted above, pharmaceutically acceptable salts of the novel oxepins of this invention also are included within the scope of this invention. The term, pharmaceutically acceptable salts, is intended to include salts derived from pharmaceutically acceptable non-toxic acids and bases such as, for example, ammonium salts, alkali metal salts such as sodium and potassium salts, alkaline earth metal salts such as magnesium and calcium salts, salts of organic bases such as amine salts derived from mono-, di and triloweralkyl or loweralkanoyl amines such as trimethylamine, dimethylamine and triethanolamine, salts derived from heterocyclic amines such as piperidine, 1-methylpiperazine, piperazine and morpholine, and salts derived from pharmaceutically acceptable acids such as hydrochloric acid, sulfuric acid, tartaric acid and propionic acid.

The oxepins of formula I and IA are useful in the treatment and prophylaxis of human or warm-blooded animal disease conditions where excessive undesirable contractile activity of prostaglandins, such as $PGF_{2\alpha}$, or prostaglandin biosynthetic intermediates contribute.

In particular, they are of value in the treatment and control of allergic conditions such as asthma.

The magnitude of a prophylactic or therapeutic dose of compound of formula I and IA will, of course, vary with the nature and the severity of the condition to be treated and with the particular compound of formula I and IA and its route of administration. In general, the dose range lies within the range of 0.2 mg. to 100 mg. per kg. body weight per day.

The pharmaceutical compositions of the present invention comprise a compound of formula I and IA as an active ingredient, and may also contain pharmaceutically acceptable carrier and optionally other therapeutic ingredients. The compositions include compositions suitable for oral, rectal, opthalmic, pulmonary, nasal, dermal, topical or parenteral (including subcutaneous, intramuscular and intravenous) administration, although the most suitable route in any given case will depend on the nature and severity of the condition being treated and on the nature of the active ingredient. They may be conveniently presented in unit dosage form and prepared by any of the methods well known in the art of pharmacy.

For use where a composition for intravenous administration is employed, a suitable dosage range is from 0.2 to 25 mg. (preferably 2 to 15 mg) of a compound of formula I and IA per kg. of body weight per day and in the case where an oral composition is employed a suitable dosage range is about, e.g., 1 to 60 mg. of a compound of formula I and IA per kg. of body weight per day, preferably from 10 to 40 mg./kg.

Pharmaceutical compositions of the present invention suitable for oral administration and by inhalation in the case of asthma therapy may be presented as discrete units such as capsules, cachets or tablets each containing a pre-determined amount of the active ingredient; as a powder or granules; or as a solution or a suspension in an aqueous liquid, or a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or moulding, optionally with one or more accessory ingredients. Compressed tablets may be prepared by compressing in a suitable machine, the active ingredient in a free-flowing form such as powder or granules, optionally mixed with a binder, lubricant, inert diluent, lubricating, surface active or dispersing agent. Moulded tablets may be made by moulding in a suitable machine, a mixture of powdered compound moistened with an inert liquid diluent. Desirably, each tablet contains from 50 mg. to 500 mg. of the active ingredient and each cachet or capsule contains from 50 mg. to 500 mg. of the active ingredient.

The best mode contemplated by applicants for carrying out their invention is illustrated in the following working examples. No limitation, however, is intended except as set forth in the appended claims.

EXAMPLE 1

6,11-Dihydro-11-oxodibenz[b,e]oxepin-2-carboxylic acid

Step A: Methyl α-Bromo-o-toluate

Heat a mixture of 41 gm. (0.3 mole) of o-toluic acid and 100 cc. of thionyl chloride at 60°-70° C. for 1 hour. Remove excess thionyl chloride by co-evaporation with benzene. Dissolve the residue (the acid chloride) in 60 cc. of benzene and add this solution at a rapid dropwise rate to 300 cc of methanol. Stir the mixture for 1 hour and remove the solvent by evaporation. Dissolve the residue (the methyl ester) in 500 cc. of carbon tetrachloride. Add 59 gm. of N-bromosuccinimide (10% excess) and reflux for 7 hours. Cool the mixture, filter and strip the filtrate to a yellow oil. This crude methyl α-bromo-o-toluate (68 gm.) is used without further purification in the next step.

Step B: Methyl o-(p-bromophenoxymethyl)benzoate

Wash 15.12 gm (0.315 mole) of sodium hydroxide, 50% dispersion in oil, free of oil with hexane and suspend in 250 cc. of N,N-dimethylformamide. Add 54.5 gm. (0.315 mole) of p-bromophenol in portions as hydrogen is evolved. After gas evolution has subsided, add a solution of 68 gm. (0.3 mole) of methyl α-bromo-o-toluate in 50 cc. of N,N-dimethylformamide at a rapid dropwise rate. Stir the mixture for 45 minutes and pour into 3 liters of cold water. Separate the solids by filtration, wash with water and dry to obtain 90 gm. of crude methyl o-(p-bromophenoxymethyl)benzoate which is used in the next step without further purification.

Step C: o-(p-Bromophenoxymethyl)benzoic Acid

Reflux 90 gm. of the crude methyl o-(p-bromophenoxymethyl)benzoate from Step B for 1 hour in a mixture of 500 cc. of methanol and 250 cc. of 10% aqueous sodium hydroxide. Evaporate the methanol and dilute the resulting aqueous solution with an equal volume of water. Acidify with conc. hydrochloric acid. Separate the solids by filtration, wash with water and dry in vacuo to obtain the title product (m.p. 183°-185° C.).

Step D: 2-Bromo-6,11-dihydro-11-oxodibenz[b,e]oxepin

Reflux 120 gm. of o-(p-bromophenoxymethyl)benzoic acid in 500 cc. of trifluoroacetic anhydride containing 0.5 cc. of boron trifluoride-ether complex for 3½ hours. Cool, separate the solids by filtration, and wash with ether in order to obtain the title product (m.p. 136°-139° C.).

Step E: 2-Cyano-6,11-dihydro-11-oxodibenz[b,e]oxepin

Reflux 43 gm. (0.1488 mole) of 2-bromo-6,11-dihydro-11-oxodibenz[b,e]oxepin and 16 gm. (0.178 mole, 20% excess) of cuprous cyanide in 150 cc. of N,N-dimethylformamide for 24 hours. Cool to 100° C. and pour into a solution of 100 gm. of ferric chloride in 140 cc. of 5% aqueous hydrochloric acid with stirring. Keep the mixture at 70° C. for 30 minutes cool, filter and wash the solids with water. Dissolve the solids in methylene chloride and purify by filtering through a short column of silica gel (m.p. 160°-161° C.).

Step F: 6,11-Dihydro-11-oxodibenz[b,e]oxepin-2-carboxylic acid

Reflux 27.3 gm. of 2-cyano-6,11-dihydro-11-oxodibenz[b,e]oxepin in a mixture of 300 cc. of 37% aqueous hydrochloric acid and 300 cc. of glacial acetic acid for 24 hours. Cool, dilute with water and separate the solids by filtration in order to obtain the title product (m.p. 250° C. dec.).

EXAMPLE 2

6,11-Dihydro-11-oxodibenz[b,e]oxepin-9-carboxylic Acid

Step A: 5-Bromo-o-toluic Acid

Chill a mixture of 140 gm. (0.875 mole) of bromine and 2.45 gm. of iron powder in an ice-bath and add portionwise during 15 minutes 93.31 gm. (0.7 mole) of o-toluic acid. Remove the reaction flask from the ice-bath and stir for 2 hours. Allow the resulting mushy solid to stand at room temperature overnight. Flush the reaction mixture with nitrogen. Finely grind the resulting solid cake, wash with water, aqueous sodium thiosulfate solution, water and dry to obtain the title compound together with the 3-bromo isomer (yield 144.7 gm., m.p. 112°-148° C.). The product is employed in the next step without further purification.

Step B: Methyl 5-Bromo-o-toluate

Reflux a mixture of 54.30 gm. (0.252 mole) of 5-bromo-o-toluic acid, 400 ml. of methanol and 5 ml. of concentrated sulfuric acid for 18.5 hours. Remove the methanol under vacuum. Dissolve the residue in benzene, wash with water, aqueous sodium bicarbonate solution, water and dry over anhydrous magnesium sulfate. Remove the solvent under vacuum and distill the residual oil to obtain the title product together with the 3-bromo isomer as a colorless oil (yield 41.6 gm., b.p. 132°-135° C./0.1 mm). Chill the oil in a refrigerator for 1 hour and separate the solids to obtain 12.53 gm. of white solid (m.p. 42°-46° C., mainly the 5-bromo isomer).

Step C: Methyl 5-Bromo-α-phenoxy-o-toluate

Treat a solution of 17.48 gm. (0.0763 mole) of methyl 5-bromo-o-toluate in 85 ml. of carbontetrachloride portionwise during 30 minutes with a mixture of 14.26 gm. (0.0801 mole) of N-bromosuccinimide and 152 mg. of benzoyl peroxide. Heat the resulting mixture under reflux for 3 hours. Cool to room temperature and separate the succinimide by filtration. Remove the solvent under vacuum to obtain methyl α,5-dibromo-o-toluate as a yellow residual oil. Heat a mixture of 7.18 gm. (0.0763 mole) of phenol, 85 ml. of dimethylformamide, 31.63 gm. (0.2289 mole) of potassium carbonate and the methyl α,5-dibromo-o-toluate obtained above at 55°–60° C. for 2 hours. Cool the mixture and pour into 350 ml. of water. Extract the resulting oil into ether, wash with water and dry over anhydrous magnesium sulfate. Remove the solvent under vacuum and allow the residual oil (24.51 gm.) to stand overnight. Separate the solids formed by placing the mixture on porous plates. Wash the solids with petroleum ether to obtain the title compound [yield 13.33 gm., m.p. 69.5°–70.5° C., pmr (CDCl$_3$) 3.90(3H, s, CH$_3$O—), 5.40(2H, s, CH$_2$O—)].

Step D: 5-Bromo-α-phenoxy-o-toluic Acid

Add 13.33 gm. (0.0415 mole) of 5-bromo-α-phenoxy-o-toluate to a solution of 3.32 gm. (0.0830 mole) of sodium hydroxide in 23 ml. of water and 200 ml. of methanol and heat at reflux for 1 hour. Remove the methanol under vacuum. Dissolve the residue in 200 ml. of water and acidify with concentrated hydrochloric acid to the Congo Red end point. Remove the solids by filtration and dry to obtain the title product (yield 12.02 gm. m.p. 160°–163° C.).

Step E: 9-Bromo-6,11-dihydro-11-oxodibenz[b,e]oxepin

Stir a mixture of 11.72 gm. (0.0381 mole) of 5-bromo-α-phenoxy-o-toluic acid, 70 ml. of trifluoroacetic anhydride and 5 ml. of boron fluoride-ethyl ether complex at room temperature for 2 hours. Pour the reaction mixture into 750 ml. of ice water. Separate the solids by filtration and dry to obtain the title product (yield 10.70 gm., m.p. 101°–104° C.). Recrystallize from hexane [m.p. 107.5°–108.5° C., pmr (CDCl$_3$) 5.10(2H, s, CH$_2$O—)].

Analysis: Calculated for C$_{14}$H$_9$BrO$_2$: C, 58.16; H, 3.14; Found: C, 58.14; H, 3.27.

Step F: 6,11-Dihydro-11-oxodibenz[b,e]oxepin-9-carbonitrile

Reflux a mixture of 9.13 gm. (0.0316 mole) of 9-bromo-6,11-dihydro-11-oxodibenz[b,e]oxepin, 6.03 gm. (0.0673 mole) of cuprous cyanide and 32 ml. of dimethylformamide for 4 hours with vigorous stirring. Cool the reaction mixture and shake with a mixture of 45 ml. of chloroform, 32 ml. of saturated sodium cyanide solution and 32 ml. of water until all solids have dissolved. Separate the organic layer and wash with aqueous sodium cyanide solution and water. Dry over anhydrous magnesium dulfate. Remove the solvent to obtain the title product (yield 7.43 gm., m.p. 116°–127° C.).

Step G: 6,11-Dihydro-11-oxodibenz[b,e]oxepin-9-carboxylic Acid

Reflux a mixture of 7.43 gm. (0.0316 mole) of 6,11-dihydro-11-oxodibenz[b,e]oxepin-9-carbonitrile, 130 ml. of acetic acid, 13 ml. of water and 13 ml. of concentrated hydrochloric acid for 156 hours. Cool the reaction mixture, separate the solids by filtration and dry (yield 6.20 gm., m.p. 264°–269° C.). Recrystallize from acetic acid to obtain the title product (m.p. 270.5°–271.5° C.).

Analysis: Calculated for: C$_5$H$_{10}$O$_4$: C, 70.86; H, 3.96; Found: C, 71.08: H, 4.24.

EXAMPLE 3

6,11-Dihydro-3-isopropyl-11-oxodibenz[b,e]oxepin-9-carboxylic Acid

Step A: Methyl 5-Bromo-α-(3-isopropylphenoxy)-o-toluate

Treat a solution of 15 gm. (0.0655 mole) of methyl 5-bromo-o-toluate prepared according to Example 2 Step B in 75 ml. of carbon tetrachloride portionwise during 30 minutes with a mixture of 12.24 gm. (0.0688 mole) of N-bromosuccinimide and 130 mg. of benzoyl peroxide. Heat the resulting mixture at reflux for 3 hours. Cool to room temperature and separate the succinimide by filtration. Remove the solvent under vacuum to obtain methyl α,5-dibromo-o-toluate as a yellow residual oil. Heat a mixture of 8.92 gm. (0.655 mole) of 3-isopropylphenol, 75 ml. of dimethylformamide, 27.16 gm. (0.1965 mole) of potassium carbonate and the methyl α,5-dibromo-o-toluate obtained above at 55°–60° C. for 2 hours. Cool the mixture and pour into 350 ml. of water. Extract the resulting oil into ether, wash with water and dry over anhydrous magnesium sulfate. Remove the solvent under vacuum to obtain the title product as an orange-red residual oil [yield 23.7 gm., pmr (CDCl$_3$) 1.23 (6H,d, (CH$_3$)$_2$CH—), 2.85(1H,m, (CH$_3$)$_2$CH—), 3.90(3H,s,CH$_3$O—), 5.40 (2H,s,CH$_2$O—)].

Step B: 5-Bromo-α-(3-isopropylphenoxy)-o-toluic Acid

Add 23.79 gm. (0.0655 mole) of 5-bromo-α-(3-isopropylphenoxy)-o-toluate to a solution of 5.24 gm. (0.1310 mole) of sodium hydroxide in 35 ml. of water and 315 ml. of methanol. Heat at reflux for 3 hours. Remove the methanol under vacuum and dilute the residual solution with 300 ml. of water. Extract with ether. Separate the aqueous layer and acidify with concentrated hydrochloric acid to the Congo Red end point. Extract the resulting oil into ether, wash with water and dry over magnesium sulfate. Remove the solvent under vacuum and allow the resulting oil (21.33 gm.) to stand overnight. Wash the solids formed with petroleum ether to obtain the title compound [yield 10.94 gm., m.p. 103°–122° C., pmr (CDCl$_3$) 1.20(6H,d,(CH$_3$)$_2$CH—), 2.82(1H,m, (CH$_3$)$_2$CH—), 5.47(2H,s,CH$_2$O—), 9.18 (1H, broad s, COOH)].

Step C: 9-Bromo-6,11-dihydro-3-isopropyl-11-oxodibenz[b,e]oxepin

Stir a mixture of 9.54 gm. (0.0273 mole) of 5-bromo-α-(3-isopropylphenoxy)-o-toluic acid, 80 ml. of trifluoroacetic anhydride and 5.7 ml. of boron fluoride ethyl ether at room temperature for 2 hours. Pour the reaction mixture into 600 ml. of ice-water. Extract the resluting oil into ether, wash with water and dry over anhydrous magnesium sulfate. Remove the solvent under vacuum. Purify the resulting oil (8.96 gm.) by column chromatography on silica gel with a 1:1 mixture of benzene-cyclohexane as eluant to obtain the title product as a yellow residual oil. [yield 6.39 gm., showing a single spot, R$_f$=0.33 on thin layer chromatography on silica gel with benzene-cycloheptane (1:1) as the solvent system, pmr (CDCl$_3$) 1.20(6H,d, (CH$_3$)$_2$CH—), 2.82(1H, m, (CH$_3$)$_2$CH), 5.08(2H, s, CH$_2$O—)].

Step D: 6.11-Dihydro-3-isopropyl-11-oxodibenz[b,e]oxepin-9-carbonitrile

Reflux a mixture of 8.39 gm. (0.0253 mole) of 9-bromo-6,11-dihydro-3-isopropyl-11-oxodibenz[b,e]oxepin, 4.83 gm. (0.0539 mole) of cuprous cyanide and 30 ml. of dimethylformamide for 8 hours with vigorous stirring. Cool the reaction mixture and shake with a mixture of 36 ml. of chloroform, 25 ml. of saturated sodium cyanide solution and 25 ml. of water until all solids have dissolved. Separate the organic layer, wash with aqueous sodium cyanide solution and water and dry over anhydrous magnesium sulfate. Remove the solvent under vacuum. Purify the resulting oil (7.01 gm.) by column chromatography on silica gel with benzene as eluant to obtain the title product [yield 2.8 gm., m.p. 101°–108° C., showing a single spot, $R_f = 0.18$ on thin layer chromatography or silica gel with benzene as the solvent system, pmr (CDCl$_3$ 1,23(6H, d, (CH$_3$)$_2$CH—), 2.95 (1H,m, (CH$_3$)$_2$C$\underline{H}$—), 5.20 (2H,s, CH$_2$O)].

Step E: 6,11-Dihydro-3-isopropyl-11-oxodibenz[b,e]oxepin-9-carboxylic Acid

Reflux a mixture of 2.8 gm. (0.010 mole) of 6,11-dihydro-3-isopropyl-11-oxodibenz[b,e]oxepin-9-carbonitrile, 50 ml. of acetic acid, 5 ml. of water and 5 ml. of concentrated hydrochloric acid for 140 hours. Cool the reaction mixture, separate the solids by filtration and dry. (yield 2.07 gm., m.p. 202°–204° C.). Recrystallize from toluene to obtain the title product (m.p. 203°–204.5° C.).

Analysis: Calculated for: C$_{18}$H$_{16}$O$_4$: C,72.96; H,5.44; Found: C,73.16; H,5.62.

EXAMPLE 4

6,11-Dihydro-2,3-methylenedioxy-11-oxodibenz[b,e]oxepin-9-carboxylic Acid

Step A: Methyl 5-Bromo-α-(3,4-methylenedioxyphenoxy)-o-toluate

Treat a solution of 15.0 gm. (0.0655 mole) of methyl 5-bromo-o-toluate in 75 ml. of carbon tetrachloride portionwise during 30 minutes with a mixture of 12.83 gm. (0.0721 mole) of N-bromosuccinimide and 130 mg. of benzoyl peroxide. Heat the resulting mixture under reflux for 3 hours. Cool to room temperature and separate the succinimide by filtration. Remove the solvent under vacuum to obtain methyl α,5-dibromo-o-toluate as a yellow residual oil. Heat a mixture of 9.05 gm. (0.0655 mole) of 3,4-methylenedioxyphenol, 75 ml. of dimethylformamide, 27.16 gm. (0.1965 mole) of potassium carbonate and the methyl α,5-dibromo-o-toluate obtained above at 55°–60° C. for 2 hours. Cool the mixture and pour into 350 ml. of water. Extract the resulting oil into ether, wash with water and dry over anhydrous magnesium sulfate. Remove the solvent under vacuum to obtain the title product as a waxy solid (yield 23.92 gm.). Recrystallize from cyclohexane to obtain pure product as yellow needles [yield 16.12 gm. m.p. 93°–98° C., pmr (CDCl$_3$) 3.88 (3H,s, CH$_3$O—), 5.30 (2H,s,CH$_2$O—), 5.85 (2H, s,OCH$_2$O—)].

Step B: 5-Bromo-α-(3,4-methylenedioxyphenoxy)-o-toluic Acid

Add 16.07 gm. (0.044 mole) of methyl 5-bromo-α-(3,4methylenedioxyphenoxy)-o-toluate to a solution of 3.52 gm. (0.088 mole) of sodium hydroxide in 24 ml. of water and 212 ml. of methanol. Heat the mixture under reflux for 1 hour. Remove the methanol under vacuum and dissolve the residue in 225 ml. of water. Acidify with concentrated hydrochloric acid to the congo red end point. Separate the solids by filtration and dry (yield 14.14 gm., m.p. 167°–177° C.). Recrystallize from ethanol-water to obtain pure product as tan needles (m.p. 177°–180° C.).

Step C: 9-Bromo-6,11-dihydro-2,3-methylenedioxy-11-oxo-dibenz[b,e]oxepin

Stir a mixture of 11.0 gm. (0.0313 mole) of 5-bromo-α-(3,4-methylenedioxyphenoxy)-o-toluic acid, 90 ml. of trifluoroacetic anhydride and 6 ml. of boron fluoride ethyl ether at room temperature for 23 hours. Pour the reaction mixture into 660 ml. of ice water, separate the solids by filtration and dry (yield 10.43 gm., m.p. 148°–172° C.). Recrystallize from isopropyl alcohol to obtain pure product as tan needles [m.p. 178°–180° C., pmr(CDCl$_3$) 5.05 (2H,s,CH$_2$O—), 5.97 (2H,s, OCH$_2$O—)].

Step D: 6,11-Dihydro-2,3-methylenedioxy-11-oxodibenz[b,e]oxepin-9-carbonitrile

Heat a mixture of 9.26 gm. (0.0278 mole) of 9-bromo-6,11-dihydro-2,3-methylenedioxy-11-oxodibenz[b,e]oxepin, 5.23 (0.0584 mole) of cuprous cyanide and 33 ml. of dimethylformamide under reflux for 9 hours with vigorous stirring. Cool the reaction mixture and shake with a mixture of 45 ml. of chloroform, 32 ml. of saturated sodium cyanide solution and 32 ml. of water until all solids have dissolved. Separate the organic layer, wash with aqueous sodium cyanide solution and water and dry over anhydrous magnesium sulfate. Remove the solvent under vacuum to obtain the title product (yield 7.76 gm., m.p. 217°–220° C.). Recrystallize from acetic acid to obtain pure product as tan prisms [m.p. 224°–225° C., pmr (CDCl$_3$) 5.03 (2H,s, CH$_2$O), 617(2H,s,OCH$_2$O—)].

Step E: 6,11-Dihydro-2,3-methylenedioxy-11-oxodibenz[b,e]oxepin-9-carboxylic Acid Heat a mixture of 4.98 gm. (0.0178 mole) of 6,11-dihydro-2,3-methylenedioxy-11-oxodibenz[b,e]-oxepin-9-carbonitrile, 90 ml. of acetic acid, 9 ml. of concentrated hydrochloric acid under reflux of 74 hours. Cool the reaction mixture and separate the solids by filtration and dry (yield 3.45 gm.). Suspend the solids in water and treat with N-methylpiperazine. Remove base insolubles by filtration and acidify the filtrate with concentrated hydrochloric acid to the Congo Red end point. Separate the solids by filtration and dry. Purify by recrystallization from acetic acid to obtain the title product (m.p. 320°–321° C.)

Anaylsis: Calculated for C$_{16}$H$_{10}$O$_6$: C,64.43; H, 3.38; Found: C,64.58; H, 3.53.

EXAMPLE 5

2-(1H-Tetrazol-5-yl)-6,11-dihydro-11-oxodibenz[b,e]oxepin

Heat a mixture of 25 gm. (0.106 mole) of 2-cyano-6,11-dihydro-11-oxodibenz[b,e]oxepin, 8.28 gm. (0.127 mole of sodium azide and 7.37 gm. (0.138 mole of ammonium chloride in 250 ml. of N,N-dimethylformamide to 140° C. for 27 hours. Cool, dilute with 500 cc. of water and acidify with 20% aqueous hydrochloric acid. Separate the solids by filtration and crystallize from ethanol to obtain the title product (m.p. 248° C. dec.).

EXAMPLE 6

9-(1H-Tetrazol-5-yl)-6,11-Dihydro-11-oxodibenz[b,e]oxepin

Heat a mixture of 800 mg. of the nitrile of Example 2, Step F, 293 mg. of sodium azide and 265 mg. of ammonium chloride in 25 ml. of dimethylformamide at 130°–135° C. for 6 hours. Dilute the mixture with water and excess sodium carbonate. Extract with ethyl acetate. Acidify the aqueous phase and separate and precipitate by filtration to obtain the title product.

EXAMPLE 7

2-(3-Hydroxy-1,2,5-thiadiazol-4-yl)-6,11-dihydro-11-oxodibenz[b,e]oxepin

Step A: 6,11-Dihydro-11-oxodibenz[b,e]oxepin-2-carboxaldehyde

Heat a mixture of 5.0 gm. of 2-cyano-6.11-dihydro-11-oxodibenz[b,e]oxepin and 4.0 gm. of Raney nickel alloy in 60 ml. of 75% (v/v) aqueous formic acid at reflux for 1.5 hours. Cool to room temperature and filter. Concentrate to small volume and extract with methylene chloride. Wash the extract with water and with 1 N sodium bicarbonate until neutral. Dry the neutral extract over sodium sulfate and concentrate to dryness to obtain the title product.

Step B: 2-Amino-2-(6,11-Dihydro-11-oxodibenz[b,e]oxepin-2-Yl)acetonitrile

Stir at room temperature for 12 hours a mixture of 5.85 gm. of ammonium chloride, 5.3 gm. of sodium cyanide, 75 ml. of ammonium hydroxide, 100 ml. of ethanol saturated with ammonia and 12 gm. of the carboxaldehyde of Step A. Pour the reaction mixture into 300 ml. of water and extract with ether. Dry the extract over sodium sulfate and concentrate to dryness to obtain the title product.

Step C: 2-amino-2-(6,11-Dihydro-11-oxodibenz[b,e]oxepin-2-Yl)acetamide

Stir at room temperature 5.0 gm. of the aminoacetonitrile of Step B in 30 ml. of concentrated hydrochloric acid for 30 minutes. Slowly pour the reaction mixture into cold ammonium hydroxide. Extract the mixture with ether and dry over sodium sulfate. Evaporate the extract to dryness to obtain the title product.

Step D: 2-(3-Hydroxy-1,2,3-thia diazol-4-yl)-6,11-dihydro-11-dibenz[b,e]oxepin

Stir overnight at room temperature a mixture of 2.365 gm. of the aminoacetamide of Step C, 1.989 gm. of sulfur monochloride and 5 ml. of dimethylformamide. Filter the reaction mixture and then partition between ice-water (75 ml.) and ethyl acetate (75 ml.). Filter, separate the organic layer, wash with saturated aqueous sodium chloride solution and dry over magnesium sulfate. Evaporate to dryness and dissolve the residue in 200 ml. of boiling ethanol, treat with charcoal and filter. Concentrate to 25 ml., and separate the solids by filtration to obtain the title product (mp. 275°–278° C.).

By substituting 9-cyano-6,11-dihydro-11-oxodibenz[b,e]oxepin for the 2-cyano-6,11-dihydro-11-oxodibenz[b,e]oxepin employed in Step A, above, there is obtained the corresponding 9-(3-hydroxy-1,2,5-thiadiazol-4-yl)-6,11-dihydro-11-oxodibenz[b,e]oxepin.

EXAMPLE 8

2-(4-Hydroxy-$\Delta^3$-pyrrolin-2,5-dione-3-yl)-6,11-dihydro-11-oxodibenz[b,e]oxepin Step A: 4-(2-Carboxybenzyloxy)phenylacetic Acid Prepare the disodium salt of p-hydroxyphenylacetic acid by mixing 15 ml. of 40% aqueous sodium hydroxide and 11.41 gm. of p-hydroxyphenylacetic acid. Evaporate the mixture to dryness and treat with benzene to eliminate residual water. Evaporate to dryness. Stir the solid residue with 10 gm. of phthalide at 180° C. for 30 minutes, then at 210° C. for 2.5 hours. Cool and dissolve in 300 ml. of water. Acidify with hydrochloric acid and separate the precipitate by filtration to obtain the title product as a cream colored solid (m.p. 171°–174° C. lit. 181°–183° C., cryst.).

Step B: 6,11-Dihydro-11-oxodibenz[b,e]oxepin-2-acetic Acid

Suspend 12 gm. of the carboxybenzyloxyphenylacetic acid of Step A in 50 ml. of trifluoroacetic anhydride in a pressure bottle and stir at 70° to 80° C. for 2.25 hours. Evaporate the reaction mixture to a syrup. Dissolve in 50 ml. of tetrahydrofuran and treat with sodium carbonate until pH 8. Stir for 15 minutes and acidify with 5 N HCl. Dilute with water and extract with ether. Wash the extract with water and dry over magnesium sulfate. Concentrate to dryness and recrystallize from ethyl acetate/hexane to obtain the title product.

Step C: 6,11-Dihydro-11-oxodibenz[b,e]oxepin-2-acetamide

Reflux for 20 minutes a mixture of 5.0 gm. of the acid from Step B and 40 ml. of thionyl chloride. Evaporate to dryness under vacuum. Evaporate twice with 30 ml. portions of carbon tetrachloride. Dissolve the residue in 20 ml. of tetrahydrofuran and add the solution dropwise to a cooled and stirred saturated solution (ice-bath) of ammonia in 60 ml. of tetrahydrofuran. Pass ammonia through the solution simultaneously. Continue stirring at room temperature for an additional 15 minutes. Evaporate the mixture to dryness. Add a mixture of 12 ml. of ethanol and 60 ml. of water and stir the suspension for 30 minutes. Separate the solids, wash with water, then with ethanol and finally with ether to obtain the title product.

Step D: 2-(4-Hydroxy-$\Delta^3$-pyrrolin-2,5-dione-3-yl)6,11-dihydro-11-oxodibenz[b,e]oxepin Stir at room temperature a mixture of 5.118 gm. of the amide of Step C, 2.939 gm. of diethyl oxalate, 4.723 gm. of potassium t-butoxide and 40 ml. of dimethylformamide for 6 hours. Pour the reaction mixture into 300 ml. of ice-water and extract with 300 ml. of ethyl acetate. Acidify with 6 N hydrochloric acid and extract with ethyl acetate. Wash with saturated aqueous sodium chloride solution and dry over magnesium sulfate. Evaporate to dryness and dissolve the residue in warm water dioxane. Treat with a slight excess of concentrated ammonium hydroxide and separate the solids by filtration. Wash with dioxane and dry. Suspend the solid in water (400 ml.). Acidify with 6 N hydrochloric acid and extract with ethyl acetate. Wash the extract with saturated aqueous sodium chloride solution, dry over magnesium sulfate and evaporate to about 15 ml. Heat the residue to boiling and allow to stand at room temperature for 1 hour. Separate the solid by filtration and wash with ethyl acetate to obtain the title product (m.p. 278°–280° C. dec.).

EXAMPLE 9

9-(4-Hydroxy-$\Delta^3$-pyrrolin-2,5-dione-3-yl)-6,11-dihydro-11-oxodibenz[b,e]oxepin Step A: 2-Phenoxymethyl-5-methylbenzoic Acid Stir a mixture of 1.0 gm of 6-methylphthalide and 0.64 gm of sodium phenolate at a temperature of 200°–210° C. for 1 hour. Cool and dissolve the reaction mixture in water. Acidify with 5% hydrochloric acid and extract with ether. Evaporate to dryness and chromatograph the residue over silica gel eluting with chloroform/methanol (50:1). Evaporate the eluate to dryness and crystallize the residue from ethyl acetate/benzene to obtain the title product.

Step B: 9-Methyl-6,11-dihydro-11-oxodibenz[b,e]oxepin

Mix 0.2 gm of the phenoxymethylbenzoic acid of Step A, 1 ml of thionyl chloride and 10 ml of dry benzene. Reflux for 1 hour and concentrate to dryness in vacuo. Dissolve the residue in 10 ml of dry 1,2-dichloroethane and add 0.3 gm of anhydrous aluminum chloride while stirring in an ice bath. After 10 minutes, pour the reaction mixture into ice water, extract with chloroform, wash with water and dry over magnesium sulfate. Concentrate to dryness and chromatograph the residue over silica gel eluting with chloroform. Concentrate the eluate to dryness and crystallize from hexane to obtain the title product.

Step C: 9-Bromomethyl-6,11-dihydro-11-oxodibenz[b,e]oxepin

To a stirred and irradiated (Tungsten lamp) solution of 2.0 gm of the 9-methyl compound of Step B in 5 ml of 1,2-dibromoethane, add a solution of 1.7 gm of bromine in 5 ml of 1,2-dibromoethane dropwise over a period of 1 hour at 150° C. Cool the reaction mixture, pour into ice water and extract with water and dry over sodium sulfate. Concentrate to dryness and crystallize the residue from isopropyl ether to obtain the title product.

Step D: 9-Cyanomethyl-6,11-dihydro-11-oxodibenz[b,e]oxepin

Dissolve 6.4 gm of the bromomethyl compound of Step C in 75 cc of dimethylformamide and add 2.95 gm of sodium cyanide. Stir the mixture at room temperature for 1.5 hours. Dilute with 600 cc of water and extract three times with ether. Wash the combined organics with water, dry and strip to a solid residue. Triturate in hexane and recover the solid by filtration.

Step E: 6,11-Dihydro-11-oxodibenz[b,e]oxepin-9-acetic Acid

Reflux 2.0 gm of the nitrile of Step D in a mixture of 30 cc of 20% aqueous sodium hydroxide and 30 cc of ethanol for four hours. Strip away the alcohol, wash with ethyl acetate and acidify the aqueous phase with hydrochloric acid. Separate the precipitate by filtration. Wash with water and dry.

Step F: 6,11-Dihydro-11-oxodibenz[b,e]oxepin-9-acetamide

Reflux for 20 minutes a mixture of 5.0 gm of the acid of Step E and 40 ml of thionyl chloride. Evaporate to dryness under vacuum. Evaporate twice with 30 ml portions of carbon tetrachloride. Dissolve the residue in 20 ml of tetrahydrofuran and add the solution dropwise to a cooled and stirred saturated solution (ice-bath) of ammonia in 60 ml of tetrahydrofuran. Pass ammonia through the solution simultaneously. Continue stirring at room temperature for an additional 15 minutes. Evaporate the mixture to dryness. Add a mixture of 12 ml of ethanol and 60 ml of water and stir the suspension for 30 minutes. Separate the solids and wash with water, then with ethanol and finally with ether to obtain the title product.

Step G: 2-(4-Hydroxy-Δ³-pyrrolin-2,5-dione-3-yl)6,11-dihydro-11-oxodibenz[b,e]oxepin Stir at room temperature a mixture of 5.118 gm of the amide of Step F, 2.939 gm of diethyl oxalate, 4.723 gm of potassium t-butoxide and 40 ml of dimethylformamide for 6 hours. Pour the reaction mixture into 300 ml of ice-water and extract with 300 ml of ethyl acetate. Acidify with 6 N hydrochloric acid and extract with ethyl acetate. Wash with saturated sodium chloride solution and dry. Evaporate to dryness and dissolve the residue in warm dioxane. Treat with a slight excess of ammonia and separate the solid by filtration. Wash with dioxane and dry. Suspend the product in water, acidify with 6 N hydrochloric acid and extract with ethyl acetate. Wash the extract with saturated sodium chloride solution, dry over magnesium sulfate and evaporate to obtain the title product.

EXAMPLE 10

Methyl 6,11-Dihydro-11-oxodibenz[b,]oxepin-9-carboxylate

Step A: 9-Chlorocarbonyl-6,11-dihydro-11-oxodibenz[b,e]oxepin

Dissolve 5.16 of 6,11-dihydro-11-oxodibenz[b,e]oxepin-9-carboxylic acid in 100 cc. of chloroform and 50 cc. of thionyl chloride and add to the mixture 1.0 cc. of dimethylformamide. Allow the mixture to stand at room temperature for 72 hours. Evaporate the mixture to dryness to obtain the desired acid chloride.

Step B: Methyl 6,11-Dihydro-11-oxodibenz[b,e]oxepin-9-carboxylate

Dissolve 2.0 gm of the acid chloride of Step A in 20 cc. of tetrahydrofuran containing 1.0 cc. of methanol and 4 cc. of pyridine. Allow the mixture to stand at room temperature for 24 hours then evaporate to dryness. Dissolve the residue in 1:4 ether/hexane and filter through silica gel. Evaporate the filtrate to dryness to obtain the title product.

Employing the process of Example 16, but substituting another lower alkanol such as, for example, ethanol, 2-propanol, n-butanol and 2-butanol for the methanol of Step B, the corresponding lower alkyl esters of 6,11-dihydro-11-oxodibenz[b,e]oxepin-9-carboxylic acid are obtained.

EXAMPLE 11

Methyl 6,11-Dihydro-11-oxodibenz[b,e]oxepin-2-carboxylate

Repeat the process of Example 10, substituting 6,11-dihydro-11-oxodibenz[b,e]oxepin-2-carboxylic acid for the 6,11-dihydro-11-oxodibenz[b,e]oxepin-2-carboxylic acid of Step A, in order to obtain the title product. By substituting, where desired, other lower alkanols such as, for example, ethanol, 2-propanol, butanol and 2-butanol, for the methanol of Step B, the corresponding lower alkyl esters of 6,11-dihydro-11-oxodibenz[b,e]oxepin-2-carboxylic acid are obtained.

EXAMPLE 12

6,11-Dihydro-11-oxodibenz[b,e]oxepin-2-carboxamide

Step A: 2-Chlorocarbonyl-6,11-dihydro-11-oxodibenz[b,e]oxepin

Heat a solution of 5 gm. of 6,11-dihydro-11-oxodibenz[b,e]oxepin-2-carboxylic acid and 40 ml. of thionyl chloride under reflux for 20 minutes. Evaporate the reaction mixture under vacuum to dryness. Repeat the evaporation with two 30 ml. portions of carbon tetrachloride. Crystallize the residue from diisopropyl ether to obtain the title product.

Step B: 6,11-Dihydro-11-oxodibenz[b,e]oxepin-2-carboxamide

Dissolve the acid chloride from Step A in 20 ml. of dry tetrahydrofuran and add this solution dropwise with stirring to a cooled (ice-bath) saturated solution of ammonia in 60 ml. of tetrahydrofuran. Pass ammonia through the reaction mixture simultaneously for 15 minutes. Stir at room temperature for an additional 15 minutes and evaporate the reaction mixture to dryness. Add a mixture of 12 ml. of ethanol and 60 ml. of water to the residue and stir at room temperature for an additional 30 minutes. Separate the solid by filtration and wash with water, then with ethanol and then with ether. Dry in vacuo to obtain the title product.

In a similar manner, substituting 6,11-dihydro-11-oxodibenz[b,e]oxepin-9-carboxylic acid for the 6,11-dihydro-11-oxodibenz[b,e]oxepin-2-carboxylic acid in Step A, there is obtained 6,11-dihydro-11-oxodibenz[b,e]oxepin-9-carboxamide.

EXAMPLE 13

6,11-Dihydro-11-oxodibenz[b,e]oxepin-2-N-Methylcarboxamide

Add 6.0 gm of 2-chlorocarbonyl-6,11-dihydro-11-oxodibenz[b,e]oxepin to 4 gm of methylamine in 100 ml of methylene chloride at 0°–5° C. Add 13 ml of triethylamine dropwise over 10 minutes then stir the reaction mixture at room temperature overnight. Extract the reaction mixture with water, dry the organic layer, and evaporate to dryness. Chromatograph over silica gel eluting with 200:20 toluene/dioxane. Evaporate eluate to dryness and recrystallize residue from methanol to obtain the title product.

In a similar manner, substituting another N-loweralkylamine such as, for example, ethylamine, propylamine, isopropylamine, butylamine and the like, or a N,N-di-loweralkylamine such as, for example, dimethylamine, diethylamine, dipropylamine, dibutylamine and the like, for the methylamine employed above, there is obtained the corresponding 6,11-dihydro-11-oxodibenz[b,e]oxepin-2-N-loweralkylcarboxamide or 2-N,N-di-loweralkylcarboxamide. Corresponding 6,11-dihydro-11-oxodibenz[b,e]oxepin-9-carboxamides, 9-N-loweralkylcarboxamides and 9-N,N-di-loweralkylcarboxamides are prepared by substituting 9-chlorocarbonyl-6,11-dihydro-11-oxodibenz[b,e]oxepin for the 2-chlorocarbonyl-6,11-dihydro-11-oxodibenz[b,e]oxepin employed above.

Also in a similar manner, substituting a carboxyloweralkylamine such as, for example, glycine, valine, leucine, isoleucine and the like, or the N-loweralkyl derivatives thereof, such as for example, N-methylglycine, N-propyleucine, N-butylisoleucine and the like, there is obtained the corresponding 6,11-dihydro-11-oxodibenz[b,e]oxepin-9(or 2)-carboxyloweralkylcarboxamides or the N-loweralkyl derivatives thereof.

EXAMPLE 14

N-Methanesulfonyl 6,11-Dihydro-11-oxodibenz[b,e]oxepin-2-carboxamide

Heat 5.0 gm of 6,11-dihydro-11-oxodibenz[b,e]oxepin-2-carboxylic acid in 50 cc of thionyl chloride for 15 minutes at reflux and then distill off the excess thionyl chloride. Evaporate the residue twice with small volumes of benzene. Add the resulting acid chloride to 4.0 gm of methanesulphonamide in 100 ml of methylene chloride at 0°–5° C. Add dropwise over 10 minutes 15 ml of triethylamine. Stir the mixture at room temperature overnight. Extract the reaction mixture with 100 cc of 0.5 N sodium hydroxide, wash the alkaline extract with ether and acidify with 6 N hydrochloric acid. Separate the solids by filtration and dry in vacuo over potassium hydroxide. Chromatograph over silica gel eluting with 200:20:3 toluene/dioxane/acetic acid. Evaporate the eluate to dryness and recrystallize the residue from methanol to obtain the title product.

In a similar manner, substituting another loweralkylsulphonamide such as, for example, ethanesulphonamide, propanesulphonamide, butanesulphonamide and the like, for the methanesulphonamide employed above, there is obtained the corresponding N-loweralkylsulfonyl6,11-dihydro-11-oxodibenz[b,e]oxepin-2-carboxamide. Corresponding 6,11-dihydro-11-oxodibenz[b,e]oxepin-9-N-loweralkylsulfonylcarboxamides are prepared by substituting 6,11-dihydro-11-oxodibenz[b,e]oxepin-9-carboxylic acid for the 6,11-dihydro-11-oxodibenz[b,e]oxepin-2-carboxylic acid employed above.

EXAMPLE 15

N-3-Methyl-2-thiazolidinylidine 6,11-Dihydro-11-oxodibenz[b,e]oxepin-2-carboxamide Reflux 1.041 gm of 6,11-dihydro-11-oxodibenz[b,e]oxepin-2-carboxylic acid in 15 cc of thionyl chloride for 30 minutes. Strip the reaction mixture to dryness and dissolve the residue in 25 cc of methylene chloride. Add a solution of 1.0 gm of 2-imino-3-methylthiazolidine in 10 cc of methylene chloride. Stir at room temperature for 30 minutes and add water. Continue stirring for 10 minutes. Separate the organic phase and wash with water and dry overnight over sodium sulfate. Strip to dryness. Stir and triturate the residue in ether, then in methanol. Chromatograph the resulting solid over silica gel, eluting with 20% ethylacetate in benzene. Strip to dryness to obtain the title product (m.p. 168°–169° C.).

EXAMPLE 16

β-Hydroxyethyl 6,11-Dihydro-11-oxodibenz[b,e]oxepin-2-carboxylate

To a stirred solution of 1.0 gm of 2-chlorocarbonyl-6,11-dihydro-11-oxo-dibenz[b,e]oxepin in 50 cc of methylene chloride, add 3 gm of ethylene glycol and stir the mixture for 18 hours at room temperature. Distill off the solvent and excess ethylene glycol under high vacuum (0.1 mm). Chromatograph the residue on a silica gel column (100 gm), eluting with 10% ethyl acetate in benzene to obtain the title product.

In a similar manner, substituting another loweralkyldiol such as, for example, trimethylene glycol and 1.4-butanediol and the like for the ethylene glycol, there is obtained the corresponding hydroxyloweralkylester. The corresponding hydroxyloweralkyl 9-carboxylate esters are prepared by substituting 9-chlorocarbonyl 6,11-dihydro-11-oxodibenz[b,e]oxepin for the 2-chlorocarbonyl 6,11-dihydro-11-oxodibenz[b,e]oxepin employed above.

EXAMPLE 17

β-Dimethylaminoethyl 6,11-Dihydro-11-oxodibenz[b,e]oxepin-9-carboxylate

Dissolve 1.0 gm of 9-chlorocarbonyl-6,11-dihydro-11-oxo-dibenz[b,e]oxepin as prepared in Example 10, Step A, in 10 cc of anhydrous tetrahydrofuran with stirring and add 2 ml of N,N-dimethylethanolamine. Stir at room temperature for 18 hours and strip the mixture to dryness. Partition the residue between ether and dilute hydrochloric acid and separate the aqueous layer. Basify the aqueous layer with aqueous ammonia and extract with ethyl acetate. Evaporate the organic phase and chromatograph the residue over silica-gel eluting with 90% chloroform in methanol to obtain the title product.

In a similar manner, substituting another N,N-diloweralkylaminoloweralkanol such as, for example, dimethylethanolamine, diethylethanolamine, 3-N,N-dimethylaminopropan-1-ol, 4-N,N-diethylaminobutan-1-ol and the like, for the N,N-dimethylethanolamine there is obtained the corresponding N,N-diloweralkylaminoloweralkyl ester. The corresponding N,N-diloweralkyl 2-carboxylate esters are prepared by substituting 2-chlorocarbonyl 6,11-dihydro-11-oxodibenz[b,e]oxepin for the 9-chlorocarbonyl-6,11-dihydro-11-oxodibenz[b,e]oxepin employed above.

EXAMPLE 18

N-Carboxyloweralkyl 6,11-Dihydro-11-oxodibenz[b,e]oxepin-2-carboxamide

Reflux 1.0 gm of 2-chlorocarbonyl-6,11-dihydro-11-oxodibenz[b,e]oxepin in 20 cc of ethyl acetate containing 2.0 gm of glycine for 5 hours. Evaporate the mixture to dryness. Add 30 cc of water to the solid residue and stir at room temperature for one hour. Separate the solid by filtration and recrystallize from ethanol to obtain the title product.

In a similar manner, substituting another amino acid such as, for example, alanine or valine and the like for the glycine, there is obtained the corresponding 2-carboxyloweralkylcarboxamide.

The corresponding 9-carboxyloweralkylcarboxamides are prepared by substituting 9-chlorocarbonyl-6,11-dihydro-11-oxodibenz[b,e]oxepin for the 2-chlorocarbonyl-6,11-dihydro-11-oxodibenz[b,e]oxepin employed above.

EXAMPLE 19

β-Carboxyethyl 6,11-dihydro-11-oxodibenz[b,e]oxepin-2-carboxylate

Dissolve 1.0 gm of 2-chlorocarbonyl-6,11-dihydro-11-oxodibenz[b,e]oxepin in 20 cc of tetrahydrofuran and add 1.0 gm of the sodium salt of β-hydroxypropionic acid. Stir the mixture at room temperature for 18 hours. Filter and evaporate the filtrate to dryness. Recrystallize the solid residue from ethanol to obtain the title product.

In a similar manner, substituting another hydroxyloweralkanoic acid salt such as, for example, an alkali metal salt of hydroxyacetic acid, 3-hydroxybutyric acid and the like, for the β-hydroxypropionic acid sodium salt, there is obtained the corresponding carboxyloweralkyl-2-carboxylate esters. The corresponding carboxyloweralkyl-9-carboxylate esters are prepared by substituting 9-chlorocarbonyl-6,11,dihydro-11-oxodibenz[b,e]oxepin for the 2-chlorocarbonyl-6,11-dihydro-11-oxodibenz[b,e]oxepin employed above.

EXAMPLE 20

2-(1H-Tetrazol-5-yl)-6,11-dihydro-11-hydroxydibenz[b,e]oxepin

Suspend 1 gm. of 2-(1H-tetrazol-5-yl)-6,11-dihydro-11-oxodibenz[b,e]oxepin in 100 cc. of absolute ethanol and add excess sodium borohydride in portions. Dilute the resulting solution with water and acidify with aqueous conc. hydrochloric acid. Separate the solids by filtration. Crystallize from ethyl acetate to obtain the title product (m.p. 335° C.).

EXAMPLE 21

Methyl 6,11-Dihydro-11-oxodibenz[b,e]oxepin-2-carboxylate

Reflux 8 gm. of 6,11-dihydro-11-oxodibenz[b,e]oxepin-2-carboxylic acid in 600 cc. of methanol containing 1 cc. of sulfuric acid for 19 hours. Cool and separate the solids by filtration to obtain the title product. (m.p. 130°-131° C.).

To obtain an additional crop, add excess sodium bicarbonate to the filtrate, evaporate to dryness and extract the residue with chloroform.

EXAMPLE 22

6,11-Dihydro-11-hydroxydibenz[b,e]oxepin-2-carboxylic acid

Step A: Methyl 6,11-dihydro-11-hydroxydibenz[b,e]oxepin-2-carboxylate

Dissolve with warming 4.4 gm. of methyl 6,11-dihydro-11-oxodibenz[b,e,]oxepin-2-carboxylate in 500 cc. of methanol. Add in portions excess sodium borohydride. Strip the mixture to dryness and partition the residue between water and chloroform. Separate the organic phase and evaporate to obtain the title product.

Step B: 6,11-Dihydro-11-hydroxydibenz[b,e]oxepin-2-carboxylic Acid

Dissolve 900 mg. of methyl 6,11-dihydro-11-hydroxydibenz[b,e]oxepin-2-carboxylate in 20 cc. of tetrahydrofuran. Add 20 cc. 1 N aqueous sodium hydroxide. Stir at room temperature for 48 hours. Dilute with water and extract with ether. Acidify the aqueous fraction with hydrochloric acid and extract with ether. Evaporate the organic phase to obtain the title product (m.p. 275° C. dec.).

EXAMPLE 23

Methyl 6,11-Dihydro-11-chlorodibenz[b,e]oxepin-2-carboxylate

Reflux 3.14 gm. of methyl 6,11-dihydro-11-hydroxydibenz[b,e]oxepin-2-carboxylate and 15 cc. of thionyl chloride for 10 minutes. Evaporate excess thionylchloride. Remove traces of thionyl chloride by co-distillation with benzene to obtain the title product (yield 3.35 gm., 100%).

EXAMPLE 24

6,11-Dihydro-11-methylsulfonyldibenz[b,e]oxepin-2-carboxylic Acid

Step A: Methyl 6,11-Dihydro-11-methylsulfonyldibenz[b,e]oxepin-2-carboxylate

Reflux 1.4 gm. of methyl 6,11-dihydro-11-hydroxydibenz[b,e]oxepin-2-carboxylate in 6 cc. of thionyl chloride for 10 minutes. Strip away excess thionyl chloride by evaporation and dissolve the chloro intermediate so produced in 14 cc. of N,N-dimethylformamide. Add 582 mg. of methanesulfinic acid sodium salt (10% excess). Stir at room temperature for 5 days. Dilute with water and separate the solids by filtration. Crystallize from 15 cc. of benzene to obtain the title product (yield 1.18 gm. 68.6%).

Step B: 6,11-Dihydro-11-methylsulfonyldibenz[b,e]oxepin-2-carboxylic Acid

Reflux 1 gm. of the ester of Step A and 40 cc. of 1 N aqueous sodium hydroxide for 15 minutes. Strip to dryness and dissolve the residue in water. Acidify with aqueous hydrochloric acid. Separate the solids by filtration to obtain the title product (m.p. 251° C. dec.).

EXAMPLE 25

6,11-Dihydro-11-methylthiodibenz[b,e]oxepin-2-carboxylic Acid

Step A: Methyl 6,11-Dihydro-11-methylthiodibenz[b,e]oxepin-2-carboxylate

Bubble methanethiol through 40 ml. of dry dimethylformamide for about 10 minutes until the solution is saturated. Add 8.6 gm. of methyl 6,11-dihydro-11-chlorodibenz[b,e]oxepin-2-carboxylate and stir at room temperature for 20 minutes with continued bubbling of methanethiol. Stop methanethiol addition and continue stirring at room temperature for 2 hours. Dilute the reaction mixture with 500 ml. of ether and wash twice with 100 ml. of 5% aqueous potassium hydroxide. Dry over anhydrous sodium sulfate and concentrate to dryness to obtain the title product (yield 8.49 gm., 95%).

Step B: 6,11-Dihydro-11-methylthiodibenz[b,e]oxepin-2-carboxylic Acid

Suspend 4.0 gm. of the sulfide ester of Step A in a mixture of 25 ml. of methanol, 25 ml. of tetrahydrofuran and 50 ml. of 40% aqueous sodium hydroxide and reflux under a nitrogen atmosphere for 20 minutes. Cool to room temperature and pour over ice. Acidify with concentrated hydrochloric acid and extract twice with 300 ml. of methylene chloride. Wash the combined extracts with saturated aqueous sodium chloride solution, dry over anhydrous sodium sulfate and evaporate to dryness to obtain the title product (m.p. 198°-200° C.).

In a similar manner, substituting other lower alkyl thiols, such as for example ethylthiol, propylthiol, isopropylthiol, n-butylthiol and the like, for the methanethiol of Step A, corresponding 11-loweralkylthio compounds are prepared. The corresponding 9-carboxylic acids are prepared by substituting the corresponding 9-methyl carboxylate for the methyl 6,11-dihydro-11-chlorodibenz[b,e]oxepin-2-carboxylate employed above.

EXAMPLE 26

6,11-Dihydro-11-methylsulfinyldibenz[b,e]oxepin-2-carboxylic Acid

Dissolve with warming 380 mg. of 6,11-dihydro-11-methylthiodibenz[b,e]oxepin-2-carboxylic acid in 38 ml. of glacial acetic acid. Place the reaction mixture in an oil bath at 40° C. and add 1.5 ml. of 30% hydrogen peroxide. Stir the mixture at 40° C. for 3 ½ hours until the solution clears. Dilute with 300 ml. of water and separate the precipitate by filtration to obtain the title product.

EXAMPLE 27

6,11-Dihydrodibenz[b,e]oxepin-2-carboxylic Acid

Step A: Methyl 6,11-dihydrodibenz[b,e]oxepin-2-carboxylate

Reflux 4.4 gm. of methyl 6,11-dihydro-11-hydroxydibenz[b,e]oxepin-2-carboxylate with 20 ml. of thionyl chloride for 10 minutes. Evaporate excess thionyl chloride and dissolve the residue in 30 ml. of dimethylformamide. Add the mixture to a solution of 3.84 gm. of potassium tert-butoxide in 75 ml. of dimethylformamide saturated with methanethiol. Stir at room temperature for 24 hours, dilute with water and extract with ether. Evaporate to dryness and chromatograph over silica gel, eluting with toluene. Evaporate to dryness to obtain the title product as an oil (yield 3.03 gm., 84%).

Step B: 6,11-Dihydrodibenz[b,e]oxepin-2-carboxylic Acid

Dissolve 1.4 gm of the ester of Step A in 15 ml of ethanol and add 15 ml of 20% aqueous sodium hydroxide. Warm gently on a steam bath until complete solution is obtained. Strip to dryness and dissolve in water. Acidify with concentrated hydrochloric acid and separate the precipitate by filtration. Crystallize from methanol to obtain the title product (m.p. 240°-244° C.)

EXAMPLE 28

6,11-Dihydro-11-methoxydibenz[b,e]oxepin-2-carboxylic Acid

Step A: Methyl 6,11-Dihydro-11-methoxydibenz[b,e]oxepin-2-carboxylate

Mix 0.415 gm of potassium tert-butoxide, 5 ml of methanol and 5 ml of dimethylformamide and add the mixture to a solution of 1.07 gm of methyl 6,11-dihydro-11-chlorodibenz[b,e]oxepin-2-carboxylate in 40 ml of dimethylformamide. Stir at room temperature for 3 days. Dilute with water and extract with ether. Evaporate to dryness and chromatograph over silica gel with benzene as the eluting solvent to obtain the title product.

Step B: 6,11-dihydro-11-methoxydibenz[b,e]oxepin-2-carboxylic Acid

Dissolve 695 mg of the ester of Step A in 15 ml of methanol. Add 10 ml of 20% aqueous sodium hydroxide and reflux for 10 minutes. Dilute with 200 ml of water and extract with ether. Acidify the aqueous fraction with concentrated hydrochloric acid and extract into ether. Evaporate to dryness and crystallize from methanol to obtain the title product (m.p. 185° C. dec.).

EXAMPLE 29

6,11-Dihydro-11-phenylthiodibenz[b,e]oxepin-2-carboxylic Acid

Step A: Methyl 6,11-Dihydro-11-phenylthiodibenz[b,e]oxepin-2-carboxylate

Add 0.12 ml of benzenethiol to a 70° C. suspension of 0.5 gm of potassium carbonate in 5 ml of dimethylformamide. Stir under a nitrogen atmosphere for 10 minutes. Add 0.27 gm of methyl 6,11-dihydro-11-chlorodibenz[b,e]oxepin-2-carboxylic acid and stir for 15 minutes. Dilute with water and extract with ether. Wash the extract with 5% aqueous potassium hydroxide and with saturated aqueous sodium chloride solution. Dry over anhydrous sodium sulfate and concentrate to dryness to obtain the title product (Yield 0.226 gm).

Step B: 6,11-Dihydro-11-phenylthiodibenz[b,e]oxepin-2-carboxylic Acid

Dissolve 650 mg of the ester of Step A in 15 ml of methanol. Add 10 ml of 20% aqueous sodium hydroxide and reflux for 10 minutes. Dilute with 200 ml of water and extract with ether. Acidify the aqueous extract concentrated hydrochloric acid and extract into ether. Evaporate to dryness and crystalline from methanol to obtain the title product.

EXAMPLE 30

6,11-Dihydro-11-(1-imidazolyl)dibenz[b,e]oxepin-2-carboxylic Acid

Step A: Methyl 6,11-Dihydro-11-(1-imidazolyl)-dibenz[b,e]oxepin-2-carboxylate

Add 4.0 gm of methyl 6,11-dihydro-11-chlordibenz[b,e]oxepin-2-carboxylate to a 78° C. solution of 2.0 gm of imidazole in 15 ml of dimethylformamide. Stir under a nitrogen atmosphere for 1 hour. Cool to room temperature and pour into 25 ml of water. Extract twice with 125 ml of ether. Wash the combined ether extracts twice with 50 ml of water and with 25 ml of saturated aqueous sodium chloride. Dry over anhydrous sodium sulfate and evaporate to dryness to obtain the title product (Yield 3.12 gm).

Step B: 6,11-Dihydro-11-(1-imidazolyl)dibenz[b,e]oxepin-2-carboxylic Acid

Dissolve 3.1 gm of the ester of Step A in a mixture of 60 ml of methanol and 60 ml of tetrahydrofuran. Add 60 ml of 5% aqueous potassium hydroxide and heat the mixture at 70° C. under a nitrogen atmosphere for 5 hours. Pour the mixture onto ice and acidify to pH 5 with concentrated hydrochloric acid. Separate the solids by filtration. Wash with cold water and dry at 60° C. under vacuum for 2 hours to obtain the title product (m.p. 244°–255° C. dec.).

EXAMPLE 31

Methyl 6,11-dihydro-11-formamidodibenz[b,e]oxepin-2-carboxylate

Add 2.35 gm. of methyl 6,11-dihydro-11-chlorodibenz[b,e]oxepin-2-carboxylate to 20 ml. of formamide. Stir and heat the mixture at 110° C. for 3 hours. Cool to room temperature, dilute with water and separate the solids by filtration to obtain the title product (Yield 2.18 gm., 90%).

EXAMPLE 32

Methyl 6,11-dihydro-11-aminodibenz[b,e]oxepin-2-carboxylate hydrochloride

Add 600 mg. of methyl 6,11-dihydro-11-formamidodibenz[b,e]oxepin-2-carboxylate to a mixture of 20 ml. of dioxane and 24 ml. of 10% hydrochloric acid. Stir and heat the mixture at 40° C. for 18 hours. Strip to dryness and triturate the residue in tetrahydrofuran. Separate the solids by filtration. Dissolve the solids in water and basify with aqueous sodium hydroxide. Extract into ether, dry over anhydrous sodium sulfate and filter. Bubble gaseous hydrogen chloride through the solution for 15 minutes and separate the solids. Triturate in tetrahydrofuran and filter to obtain the title product (m.p. 224° C. dec.).

EXAMPLE 33

6,11-Dihydro-11-aminodibenz[b,e]oxepin-2-carboxylic Acid Hydrochloride

Heat together 340 mg. of methyl 6,11-dihydro-11-formamidodibenz[b,e]oxepin-2-carboxylate, 10 ml. of dioxane and 10 ml. of concentrated hydrochloric acid at 100° C. for 5 hours. Strip to dryness and dissolve the residue in water and pass through a Bio-Red AG-50W-X8 resin (sulfonic acid type). Collect the acid by elution with 10% ammonium hydroxide solution. Evaporate to dryness, dissolve the residue in tetrahydrofuran and acidify with aqueous hydrochloric acid. Strip to dryness and recrystallize from methanol/ether to obtain the title product (m.p. 245° dec.).

EXAMPLE 34

6,11-Dihydro-11-formamidodibenz[b,e]oxepin-2-carboxylic Acid

Add to a mixture of 1.77 gm. (5 mmole) of 6,11-dihydro-11-aminodibenz[b,e]oxepin-2-carboxylic acid in 5 ml. of 90% formic acid, 1.5 gm. of aceticformic anhydride* at 10° C. with stirring. After 1 hour allow the mixture to warm to room temperature and continue stirring for 3 hours. Remove the volatiles by evaporation in vacuo to obtain the title product.

*Acetic-formic anhydride is prepared by the method of L. Muramatsu et al., Bull. Chem. Soc. Japan, 38, 244 (1965).

EXAMPLE 35

11-Hydroxy-11-methyl-6,11-dihydrodibenz[b,e]oxepin-2-carboxylic Acid

Step A: Methyl 11-hydroxy-11-methyl-6,11-dihydrodibenz[b,e]oxepin-2-carboxylate

Dissolve 268 mg. (1 mmole) of 6,11-dihydro-11-oxodibenz[b,e]oxepin-2-carboxylic acid in 15 ml. of tetrahydrofuran. Add methyl magnesium iodide in ether solution in portions until thin layer chromatography shows only a trace of the starting carboxylic acid left. Acidify the red solution with dilute aqueous hydrochloric acid until red color disappears. Extract with ether. Separate the organic layer and chromatograph on silica gel eluting with 5% ethyl acetate/benzene to obtain the title product.

Step B: 11-Hydroxy-11-methyl-6,11-dihydrodibenz[b,e]oxepin-2-carboxylic Acid

Dissolve 450 mg. of methyl 11-hydroxy-11-methyl-6,11-dihydrodibenz[b,e]oxepin-2-carboxylate in 20 ml. of ethanol and add 20 ml. of 5% aqueous sodium hydroxide solution. Stir at room temperature for 1 hour. Evaporate the alcohol and dilute the residual sodium salt solution with 40 ml of water. Cool in an ice bath and acidify with 5N hydrochloric acid. Separate the solids by filtration and dry (yield 250 mg). Recrystallize from benzene to obtain the title product (yield 200 mg., m.p. 258°–258° C.).

EXAMPLE 36

11-Methylene-6,11-dihydrodibenz[b,e]oxepin-2-carboxylic Acid

Step A: Methyl 11-methylene-6,11-dihydrodibenz[b,e]oxepin-2-carboxylate

Dissolve 1 gm. of methyl 11-hydroxy-11-methyl-6,11-dihydrodibenz[b,e]oxepin-2-carboxylate in 100 ml. of benzene containing a few crystals of p-toluenesulfonic acid for 10 minutes. Strip the reaction mixture to dryness to obtain the title product.

Step B: 11-Methylene-6,11-dihydrodibenz[b,e]oxepin-2-carboxylic Acid

Dissolve the residue of Step A above in 40 ml. of ethanol with warming. Cool and add 40 ml. of 20% aqueous sodium hydroxide solution. Allow to stand for 2 hour and strip away the alcohol. Dilute with water and acidify with 5 N hydrochloric acid. Separate the solids by filtration and dry to obtain the title product (yield 850 mg). Purify by recrystallization from ethanol (m.p. 255°–257° C.).

EXAMPLE 37

11-Methyl-6,11-dihydrodibenz[b,e]oxepin-2-carboxylic Acid

Dissolve 514 mg of 11-methylene-6,11-dihydrodibenz[b,e]oxepin-2-carboxylic acid in 150 ml. of ethanol. Add 100 mg of 5% palladium on carbon catalyst. Hydrogenate at 20 psi for 30 minutes. Filter and strip the filtrate to dryness. Recrystallize the residue from isopropanol to obtain the title product (yield 365 mg, m.p. 224°–226° C.).

EXAMPLE 38

6,11-Dihydro-11-ethylidenedibenz[b,e]oxepin-2-carboxylic Acid

Step A: 2-Cyano-6,11-dihydro-11-ethylidenedibenz[b,e]oxepin

Suspent 23.6 gm of ethyl triphenylphosphonium bromide in 200 ml of dry tetrahydrofuran add dropwise 2.4 ml of t-butyllithium in hexane with stirring at room temperature under a nitrogen atmosphere. Continue stirring for 3 hours and then cool to −70° C. in a dry ice bath. Add 10 gm. of 2-cyano-6,11-dihydro-11-oxodibenz[b,e]oxepin in 75 ml of dry tetrahydrofuran dropwise over 30 minutes. Continue stirring at −70° C. for 30 minutes, warm to room temperature and continue stirring overnight under a nitrogen atmosphere. Pour the mixture into 400 ml. of ether, filter and wash the filtrate with saturated aqueous sodium chloride solution. Dry over anhydrous magnesium sulfate and strip to dryness. Chromatograph the residue over silica gel, eluting with 5% ethyl acetate in hexane to obtain the final product (5.73 gm).

Step B: 6,11-Dihydro-11-ethylidenedibenz[b,e]oxepin-2-carboxylic Acid

Reflux a mixture of 2.8 gm of the nitrile of Step A, 50 ml of acetic acid, 5 ml of water and 5 ml of concentrated hydrochloric acid for 140 hours. Cool the reaction mixture, separate the solids by filtration and dry. Recrystallize from toluene to obtain the title product.

In a similar manner, substituting another lower alkyl triphenylphosphonium bromide such as propyl, isopropyl or n-butyl triphenylphosphonium bromide, or benzyl or ring substituted benzyl triphenylphosphonium bromide, for the ethyl triphenylphosphonium bromide employed in Step A, above, the corresponding 11-lower alkylidene or 11-benzylidene derivatives are prepared. Where the corresponding 9-cyano-11-oxodibenz[b,e]oxepin is employed as starting material the corresponding 9-carboxylic acids are prepared. These compounds then can be reduced as described above to form the corresponding 11-loweralkyl or 11-toluyl derivatives.

What is claimed is:

1. A compound selected from the group consisting of 6,11-dihydrodibenz[b,e]oxepins having the structural formulae:

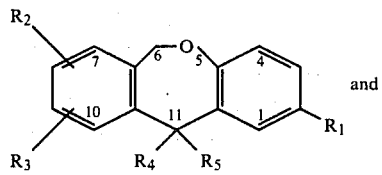

and

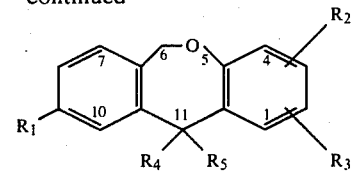

wherein
$R_2$ and $R_3$ are the same or different and are members selected from the group consisting of hydrogen, halogen, nitro, amino, N-lower alkylamino, N,N-dilower alkylamino, lower alkanoyl, hydroxy, lower alkoxy, lower alkylthio, trifluoromethylthiol, lower alkylsulfinyl, lower alkylsulfonyl and trifluoromethyl; and where $R_2$ and $R_3$ are on adjacent carbon atoms at positions 8 and 9 or 2 and 3, $R_2$ and $R_3$, taken together, are methylenedioxy;

$R_4$ is a member selected from the group consisting of hydrogen, hydroxy, loweralkoxy, lower alkylthio, lower alkylsulfinyl, lower alkylsulfonyl, phenylthio, amino, formamido, and 1-imidazolyl;

$R_5$ is a member selected from the group consisting of hydrogen and lower alkyl;

$R_4$ and $R_5$, taken together, are a member selected from the group consisting of =O and =CH-$R_7$ wherein $R_7$ is a member selected from the group consisting of hydrogen and phenyl; and $R_1$ is a member selected from the group consisting of 5-tetrazolyl and carboxy; with the proviso that $R_1$ is not 5-tetrazolyl, carboxy or carboxamido when $R_4$ and $R_5$, taken together, are =O and $R_2$ and $R_3$ are hydrogen;

and the pharmaceutically acceptable salts thereof.

2. A compound according to claim 1 wherein $R_4$ is a member selected from the group consisting of loweralkoxy, loweralkylthio, loweralkylsulfinyl, loweralkylsulfonyl and amino and $R_5$ is hydrogen; and $R_4$ is hydrogen and $R_5$ is loweralkyl; and $R_4$ and $R_5$ taken together, is methylene.

3. A compound according to claim 2 wherein $R_4$ is a member selected from the group consisting of methoxy, methylthio, methylsulfinyl, methylsulfonyl and amino and $R_5$ is hydrogen; $R_4$ is hydrogen and $R_5$ is methyl; $R_4$ and $R_5$, taken together, is methylene; $R_2$ and $R_3$ are hydrogen; and $R_1$ is a member selected from the group consisting of 5-tetrazolyl and carboxy.

4. A compound according to claim 3 wherein $R_1$ is 5-tetrazolyl; $R_4$ is hydrogen and $R_5$ is methyl.

5. A compound according to claim 3 wherein $R_1$ is 5-tetrazolyl and $R_4$ and $R_5$, taken together, is methylene.

6. A compound according to claim 3 wherein $R_1$ is 5-tetrazolyl; $R_4$ is methylthio and $R_5$ is hydrogen.

7. A compound according to claim 3 wherein $R_1$ is 5-tetrasolyl; $R_4$ is methylsulfinyl and $R_5$ is hydrogen.

8. A compound according to claim 3 wherein $R_1$ is 5-tetrazolyl; $R_4$ is methylsulfonyl and $R_5$ is hydrogen.

9. A compound according to claim 3 wherein $R_1$ is 5-tetrazolyl; $R_4$ is methoxy and $R_5$ is hydrogen.

10. A compound according to claim 3 wherein $R_1$ is 5-tetrazolyl, $R_4$ is amino and $R_5$ is hydrogen.

11. A compound according to claim 3 wherein $R_1$ is carboxy; $R_4$ is hydrogen and $R_5$ is methyl.

12. A compound according to claim 3 wherein $R_1$ is carboxy and $R_4$ and $R_5$, taken together, is methylene.

13. A compound according to claim 3 wherein $R_1$ is carboxy; $R_4$ is methylthio and $R_5$ is hydrogen.

14. A compound according to claim 3 wherein $R_1$ is carboxy; $R_4$ is methylsulfinyl and $R_5$ is hydrogen.

15. A compound according to claim 3 wherein $R_1$ is carboxy; $R_4$ is methylsulfonyl and $R_5$ is hydrogen.

16. A compound according to claim 3 wherein $R_1$ is carboxy, $R_4$ is methoxy and $R_5$ is hydrogen.

17. A compound according to claim 3 wherein $R_1$ is carboxy, $R_4$ is amino and $R_5$ is hydrogen.

* * * * *

UNITED STATES PATENT AND TRADEMARK OFFICE
CERTIFICATE OF CORRECTION

PATENT NO. : 4,282,365

DATED : August 4, 1981

INVENTOR(S) : Joshua Rokach et al

It is certified that error appears in the above—identified patent and that said Letters Patent is hereby corrected as shown below:

On the face of the patent under "Assignee", please insert underneath "Merck & Co., Inc., Rahway, N. J.", insert the additional assignee of the patent -- Merck Sharp & Dohme (I.A.) Corp., Rahway, N.J. --.

In Col. 44, Claim 1, under the definition for $R_2$ and $R_3$, delete "trifluoromethylthiol" and insert therefor -- trifluoromethylthio --.

Signed and Sealed this

Seventeenth Day of November 1981

[SEAL]

Attest:

GERALD J. MOSSINGHOFF

Attesting Officer          Commissioner of Patents and Trademarks